(12) United States Patent
Galea et al.

(10) Patent No.: US 10,532,072 B2
(45) Date of Patent: Jan. 14, 2020

(54) METHOD AND COMPOSITION FOR PRODUCING ENHANCED ANTI-INFLAMMATORY/ ANTI-CATABOLIC AND REGENERATIVE AGENTS FROM AUTOLOGOUS PHYSIOLOGICAL FLUID

(71) Applicant: Antnor Limited, Toronto (CA)

(72) Inventors: Anthony Galea, Toronto (CA); Irina Brokhman, Toronto (CA)

(73) Assignee: Antnor Limited, Toronto, ON (CA)

( * ) Notice: Subject to any disclaimer, the term of this patent is extended or adjusted under 35 U.S.C. 154(b) by 75 days.

(21) Appl. No.: 15/515,996

(22) PCT Filed: Sep. 30, 2015

(86) PCT No.: PCT/CA2015/000521
§ 371 (c)(1),
(2) Date: Mar. 30, 2017

(87) PCT Pub. No.: WO2016/049746
PCT Pub. Date: Apr. 7, 2016

(65) Prior Publication Data
US 2017/0296583 A1      Oct. 19, 2017

(30) Foreign Application Priority Data

Sep. 30, 2014  (CA) ..................... 2866480
May 14, 2015  (CA) ..................... 2891445
Aug. 13, 2015  (CA) ..................... 2900537

(51) Int. Cl.
*A61K 35/14*       (2015.01)
*A61K 35/16*       (2015.01)
*C12N 9/64*        (2006.01)
*A61K 38/18*       (2006.01)
*A61K 38/20*       (2006.01)
*C07K 1/14*        (2006.01)

(52) U.S. Cl.
CPC .......... *A61K 35/14* (2013.01); *A61K 38/1841* (2013.01); *A61K 38/1858* (2013.01); *A61K 38/1866* (2013.01); *A61K 38/2006* (2013.01); *C07K 1/14* (2013.01); *C12N 9/64* (2013.01)

(58) Field of Classification Search
None
See application file for complete search history.

(56) References Cited

U.S. PATENT DOCUMENTS

2003/0138910 A1  7/2003  Reinecke et al.
2006/0177515 A1  8/2006  Schmieding
(Continued)

FOREIGN PATENT DOCUMENTS

CA   2866480 A1   3/2016
CA   2891445 A1   3/2016
(Continued)

OTHER PUBLICATIONS

Trextor ("Autologous Biologic Treatment for Equine Musculorskeletal Injuries: Platelet-Rich Plasma and IL-1 Receptor Antagonist Protein" Veterinary Clinics: Equine Practice, 2011, 27, 275-298) (Year: 2011).*
Tatarniuk ("Concentrations of Cytokines, Matrix Metalloproteinases and Tissue Inhibitors of Matrix Metalloproteinases in Autologous Conditioned Serum from Horses with Distal Interphalangeal Joint Osteoarthritis" Osteoarthritis and Cartilage, 23 (2015) (Year: 2015).*
CitraLabs ("ACD-A Anticoagulant Citrate Dextrose Solution, Solution A" available at www.citra-labs.com/products/acd-a-.cfm, webcapture on Apr. 13, 2019). (Year: 2019).*
(Continued)

*Primary Examiner* — Robert J Yamasaki
*Assistant Examiner* — Charles Zoltan Constantine
(74) *Attorney, Agent, or Firm* — TraskBritt

(57) ABSTRACT

Described are methods of producing an autologous composition useful for treatment of damaged and/or injured connective tissues, chronic tendinosis, chronic muscle tears and/or chronic degenerative joint conditions and skin inflammatory disorders in a mammal. The method comprises preparing an anti-inflammatory/anti-catabolic component of the autologous composition comprising IL-1ra and TIMPs. An anti-inflammatory/anti-catabolic component is prepared comprising: collecting blood from the mammal; delivering the blood to a tube; incubating the blood at a temperature of from about 37° C. to about 39° C. for about 24 hours, preferably in the presence of sodium citrate; centrifuging the blood to separate the blood into a supernatant component and a cellular fraction; and collecting the supernatant component. The method further comprises preparing a regenerative component of the autologous composition comprising: collecting blood from the mammal; delivering the blood to a tube in the presence of about 4% citric acid; centrifuging the blood to separate a platelet-rich plasma component from a whole blood; collecting the platelet-rich plasma component; and mixing the supernatant component with the platelet-rich plasma component to provide the autologous composition. Also provided is a method of treating damaged and/or injured connective tissues, chronic tendinosis, chronic muscle tears and/or chronic degenerative joint conditions and skin inflammatory disorders in a subject with the autologous composition, an autologous composition for treating damaged and/or injured connective tissues, chronic tendinosis, chronic muscle tears and/or chronic degenerative joint conditions and skin inflammatory disorders in a mammal and the use of the autologous composition for the treatment of damaged and/or injured connective tissues, chronic tendinosis, chronic muscle tears and/or chronic degenerative joint conditions and skin inflammatory disorders in a mammal.

15 Claims, 22 Drawing Sheets

(56) References Cited

U.S. PATENT DOCUMENTS

| | | |
|---|---|---|
| 2009/0220482 A1 | 9/2009 | Higgins et al. |
| 2010/0125236 A1 | 5/2010 | Bare et al. |
| 2010/0125336 A1 | 5/2010 | Johnson et al. |
| 2014/0271587 A1 | 9/2014 | Landrigan et al. |
| 2014/0271588 A1 | 9/2014 | Landrigan et al. |
| 2014/0271589 A1 | 9/2014 | Matuska et al. |
| 2014/0274894 A1 | 9/2014 | Leach et al. |
| 2017/0296583 A1 | 10/2017 | Galea et al. |

FOREIGN PATENT DOCUMENTS

| | | |
|---|---|---|
| CA | 2900537 A1 | 3/2016 |
| CA | 2962289 A1 | 4/2016 |
| CN | 107073083 A | 8/2017 |
| EP | 3200817 A1 | 8/2017 |
| GB | 2546224 A | 7/2017 |
| JP | 2017-533896 A | 11/2017 |
| KR | 1020130027083 A | 3/2013 |
| KR | 10-2017-0063836 A | 6/2017 |
| MX | 2017004131 A | 6/2017 |
| WO | 96/18292 A1 | 6/1996 |
| WO | 2011031553 A1 | 3/2011 |
| WO | 2012030593 A2 | 3/2012 |
| WO | 2013114359 A1 | 8/2013 |
| WO | 2014149270 A1 | 9/2014 |
| WO | 2016049746 A1 | 4/2016 |

OTHER PUBLICATIONS

Wehling ("Use of Autologous Conditioned Cell-free Serum (Orthokine) in treating Osteoarthritis and Sciatic Back Pain" European Musculoskeletal Review 4: 8-11) (Year: 2009).*

Ehrenfest ("Classification of platelet concentrates: from pure platelet-rich plasma (P-PRP) to leucocyte and platelet-rich fibrin (L-PRF)", Trends in Biotechnology, 2009, vol. 27, Issue 3, 158-167). (Year: 2009).*

Ames ("An Appraisal of the "Vacutainer" System for Blood Collection", Annals of Clinical Biochemistry, 12, 1975, 151-155 (Year: 1975).*

Chevalier et al., Tissue inhibitor of metalloprotease-1 (TIMP-1) serum level may predict progression of hip osteoarthritis, Osteoarthritis and Cartilage, May 1, 2001, pp. 300-307, vol. 9, No. 4.

European Search Report for Application No. 15847588.9 dated May 23, 2018, 11 pages.

Hurme et al., IL-1 receptor antagonist (IL-1Ra) plasma levels are co-ordinately regulated by both IL-1Ra and IL-1beta genes, European Journal of Immunology, Aug. 1, 1998, pp. 2598-2602, vol. 28, No. 8.

Andia et al., Joint pathology and platelet-rich plasma therapies, 2012, Expert Opinion on Biological Therapy, vol. 12, No. 1, pp. 7-22.

Brandtaeg et al., Net inflammatory capacity of human septic shock plasma evaluated by a monocyte-based target cell assay: identification of interleukin-10 as a major functional deactivator of human monocytes. J Exp Med. J. Exp. Med. Jul. 1, 1996; 184(1):51-60.

Clarke et al., IL-10-mediated suppression of TNF-alpha production is independent of its ability to inhibit NF kappa B activity. Eur J Immunol. Eur. J. Immunol. May 1998; 28(5):1719-26.

Dinarello et al., Interleukin-1, interleukin-1 receptors and interleukin-1 receptor antagonist. Int Rev Immunol. Int. Rev. Immunol. 1998; 16(5-6):457-99.

Eming et al., Inflammation in wound repair: molecular and cellular mechanisms. J. Invest Dermatol. 2007; 127:514.

Fernandes et al., The role of cytokines in osteoarthritis pathophysiology. Biorheology. Biorheology 2002; 39 (1-2):237-46.

Fredberg et al., Chronic tendinopathy tissue pathology, pain mechanisms, and etiology with a special focus on inflammation. Scand J. Med Sci Sports. Scand. J. Med. Sci. Sports Feb. 2008; 18(1):3-15.

Fufa et al., Activation of platelet-rich plasma using soluble Type I collagen. J Oral Maxillofac Surg J. Oral Maxillofac. Surg. 2008; 66:684-90.

Gospodarowicz et al., Isolation and characterization of a vascular endothelial cell mitogen produced by pituitary-derived folliculo stellate cells. Proc. Nati. Acad. Sci. USA 86, 7311-7315, 1989.

PCT International Search Report, PCT/CA2015/000521, dated Sep. 30, 2015.

PCT International Search Report and Written Opinion, PCT/CA2015/000521, dated Sep. 30, 2015.

Lichtenauer M. et al., Phosphate buffered saline containing calcium and magnesium elicits increased secretion of interleukin-1 receptor antagonist, Laboratory Medicine, vol. 40, No. S, pp. 290-293, (2009).

Manello et al., Serum or plasma samples? The "Cinderella" role of blood collection procedures: preanalytical methodological issues influence the release and activity of circulating matrix metalloproteinases and their tissue inhibitors, hampering diagnostic trueness and leading to misinterpretation. Arterioscler Thromb Vasc Biol. Arterioscler. Thromb. Vasc. Biol. Apr. 2008;28(4):611-4.

Mirza et al., Blocking Interleukin-1β Induces a Healing-Associated Wound Macrophage Phenotype and Improves Healing in Type 2 Diabetes. Diabetes Jul. 2013; 62(7): 2579-2587.

Mishra et al., Treatment of chronic elbow tendinosis with buffered platelet-rich plasma, The American Journal of Sports Medicine, vol. 34, No. 11 pp. 1774-1778.

Mosmann et al., L. Two types of murine helper T cell clone. I. Definition according to profiles of lymphokine activities and secreted proteins. J Immunol. J. Immunol. Apr. 1, 1986; 136(7):2348-57.

Peng et al., VEGF improves, whereas sFlt1 inhibits, BMP2-induced bone formation and bone healing through modulation of angiogenesis.J Bone Miner Res. angiogenesis. J. Bone Miner. Res. Nov. 2005; 20(11):2017-27.

Poutsiaka et al., Production of interleukin-1 receptor antagonist and interleukin-1 beta by peripheral blood mononuclear cells is differentially regulated. Blood. Blood Sep. 1, 1991; 78(5)1275-81.

Sampson et al., Injection of platelet-rich plasma in patients with primary and 1-32 secondary knee osteoarthritis, 2010, American Journal of Physical Medicine and Rehabilitation, vol. 89, No. 12, pp. 961-969.

Sanchez et al., Ultrasound-guided platelet-rich plasma injections for the treatment of osteoarthritis in the hip, Nov. 10, 2011, Rheumatology, vol. 51 No. 1, pp. 144-150.

Wehling P. et al., Autologous conditioned serum in the treatment of orthopedic diseases. The Orthokine Therapy. Biodrugs. vol. 21, No. 5, pp. 323-332, (2007) ISSN: 1173-8804.

Freitag et al., The Next Step in Osteoarthritis Management—Photoactivated Platelet Rich Plasma Injections: A Case Study, Annals of the Rheumatic Disease, Jun. 2013, vol. 71, Supp. Suppl. 3. Abstract No. AB0981.

Moser et al., Intradiscal Injections of Orthokine-Derived Autologous Conditioned Serum (ACS) for Lumbar Disc Degeneration, Osteoarthritis and Cartilage, Sep. 2011, vol. 19, Supp. Suppl. 1, pp. S215. Abstract No. 464.

Patentability Search and Report that was Prepared by the Nordic Patent Institute, dated Mar. 27, 2015.

Shirokova et al., Comparison of the Efficacy of Autologous Conditioned Serum and Hyaluronic Acid Treatment in Hip OSTeoarthritis, Annals of the Rheumatic Disease, Jun. 2013 vol. 71, Supp. Suppl. 3. Abstract No. AB0981.

Office Action received for Chile Patent Application No. 2017000670, dated Oct. 3, 2018, 18 pages (8 pages of English Translation and 10 pages of Original Document).

International Search Report and Written Opinion received for PCT Patent Application No. PCT/CA2015/000521, dated Jan. 11, 2016, 13 pages.

International Preliminary Report on Patentability received for PCT Patent Application No. PCT/CA2015/000521, dated Apr. 13, 2017, 9 pages.

European Search Report and Search Opinion Received for EP Application No. 15847588.9, dated May 23, 2018, 10 pages.

Lee et al. "Anticoagulation Techniques in Apheresis: From Heparin to Citrate and Beyond" J Clin Apher. 2012; 27(3): 117-125.

(56) References Cited

OTHER PUBLICATIONS

Wright-Carpenter et al., "Treatment of Muscle Injures by Local Administration of Autologous Conditioned Serum: A Pilot Study on Sportsmen With Muscle Strains," Int J Sports Med., vol. 25, (2004), pp. 588-593.
Textor "Autologous Biologic Treatment for Equine Musculoskeletal Injuries: Platelet-Rich Plasma and IL-1 Receptor Antagonist Protein" Vet Clin North Am Equine Pract. Aug. 2011, vol. 27, Issue 2, pp. 275-298 (Abstract).
Sawyere et al., "Cytokine and Growth Factor Concentrations in Canine Autologous Conditioned Serum," Veterinary Surgery, vol. 45, (2016), pp. 582-586.
Rutgers et al., "Cytokine Profile of Autologous Conditioned Serum for Treatment of Osteoarthritis, In Vitro Effects on Cartilage Metabolism and Intra-Articular Levels After Injection," Arthritis Research & Therapy, vol. 12:R114, (2010), pp. 1-11.
Russian Search Report from Russian Patent Application No. 2017114523 (3 pages of English Translation).
Russian Office Action from Russian Patent Application No. 2017114523, (9 pages of English Translation).
Rosengren et al., "Platelet-Derived Growth Factor and Transforming Growth Factor Beta Synergistically Potentiate Inflammatory Mediator Synthesis by Fibroblast-Like Synoviocytes," Arthritis Research & Therapy, vol. 12, (2010), pp. 1-11.
Roberts et al., "TGF-(Beta): Regulation of Extracellular Matrix," Kidney International, vol. 41, (1992), pp. 557-559.
Notice of Deficiencies for Israel Patent Application No. 251082, dated May 27, 2019 (10 pages of English Translation).
Lederle et al., "Platelet-Derived Growth Factor-BB Controls Epithelial Tumor Phenotype by Differential Growth Factor Regulation in Stromal Cells," The American Journal of Pathology, vol. 169, (Nov. 2006), pp. 1767-1783.
Krishnan et al., "Multiplexed measurements of immunomodulator levels in peripheral blood of healthy subjects: Effects of analytical variables based on anticoagulants, age, and gender" Cytometry B Clin Cytom. Nov. 2014;86(6):426-35. doi: 10.1002/cyto.b.21147. Epub Feb. 26, 2014. (Abstract).
Hraha et al., Autologous Conditioned Serum: The Comparative Cytokine Profiles of Two Commercial Methods (IRAP and IRAP II) Using Equine Blood, Equine vet. J., vol. 43, (2011), pp. 516-521.
Elkington et al., "Analysis of Matrix Metalloproteinase Secretion by Macrophages," Methods Mol. Biol., vol. 531, (2009); pp. 253-265.
Biggs et al., "The Effects of Several Organic Acids on Growth Performance, Nutrient Digestibilities, and Cecal Microbial Populations in Young Chicks" Poult Sci. Dec. 2008;87(12):2581-9. doi: 10.3382/ps.2008-00080 (Abstract).
Bergin et al., "Secretion of Matrix Metalloproteinase-9 by Macrophages, In Vitro, In Response to Helicobacter Pylori," FEMS Immunology and Medical Microbiology, vol. 45, (2005), 159-169.
Japanese Notice of Reasons for Refusal for Japanese Application No. 2017-518238, dated Aug. 1, 2019, 10 pages with English translation.
Chamberlain et al. "Interleukin-1 Receptor Antagonist Modulates Inflammation and Scarring after Ligament Injury" Connect Tissue Res. vol. 55, 2014, pp. 177-186.
United Kingdom Examination Report for United Kingdom Application No. GB1706803.2, dated Sep. 17, 2019, 4 pages.

* cited by examiner

METHOD AND COMPOSITION FOR PRODUCING ENHANCED ANTI-INFLAMMATORY/ ANTI-CATABOLIC AND REGENERATIVE AGENTS FROM AUTOLOGOUS PHYSIOLOGICAL FLUID

CROSS-REFERENCE TO RELATED APPLICATIONS

This application is a national phase entry under 35 U.S.C. § 371 of International Patent Application PCT/CA2015/000521, filed Sep. 30, 2015, designating the United States of America and published in English as International Patent Publication WO 2016/049746 A1 on Apr. 7, 2016, which claims the benefit under Article 8 of the Patent Cooperation Treaty to Canadian Patent Application Serial No. 2900537 filed Aug. 13, 2015, Canadian Patent Application Serial No. 2891445 filed May 14, 2015, and Canadian Patent Application Serial No. 2866480 filed Sep. 30, 2014.

TECHNICAL FIELD

This application is directed generally to medicine and, more particularly, to methods and compositions useful in, among other things, the treatment of damaged and/or injured connective tissues including chronic tendinosis, chronic muscle tears (tendinitis), cartilage tears, chronic degenerative joint conditions such as osteoarthritis, as well as chronic inflammatory skin diseases including atopic dermatitis and chronic wounds.

BACKGROUND

Osteoarthritis ("OA") is a degenerative joint disease characterized by cartilage damage and synovial inflammation. Previous data refer to changes to a molecular inflammatory cascade that lead to a destruction of cartilage macromolecules and irreversible morphological changes.[1] Considerable evidence has shown that IL-1, Tumor Necrosis Factor-alpha, IL-6,8 and metalloproteinases are predominant catabolic and pro-inflammatory molecules playing a major role in pathogenesis of osteoarthritis.[1] These cytokines are produced by activated synoviocytes, mononuclear cells or by articular cartilage itself, and their catabolic effect can be successfully blocked by inhibitory cytokines such as IL-4, 10,13 and IL-1ra.[1]

Similar inflammatory and catabolic pathways are involved in the pathogenesis of chronic tendonitis[2] and chronic muscle tear healing failure.[3] Tendon cells are subjected to continuous damage by producing increased levels of IL-1,6, metalloproteinases (MMPs) and other catabolic molecules.[2] Pro-inflammatory cytokines IL-1 and TNF-alpha are involved in pathogenesis of chronic myositis[3] as well. Atopic dermatitis (eczema) is considered as the most common relapsing inflammatory skin conditions. Chronic wound (including diabetic wound) is a wound that does not heal within three months due to poor circulation, neuropathy, immune disorders and complications of systemic illnesses, age, and repeated trauma. All mentioned conditions are characterized by disturbing cell signaling via cytokines and lost extracellular matrix (ECM) that forms the largest component of the dermal skin layer. Targeting special inflammatory and catabolic molecular pathways can have a beneficial therapeutic effect for inflammatory pathologies. This effect could be achieved by using therapeutically active proteins. Presently, the pharmaceutical industry employs high-cost molecular genetic technologies for recombinant protein production such as insulin, interferons, blood clotting factors, etc. However, these methods of recombinant protein generation include the expression of human genes in a bacterial cell. The patterns of post-translation protein modification including glycosylation may be different than those naturally occurring in humans. This may result in instability of the product in the human environment, decreasing of biological function or immune response provocation. Additionally, the cost of the final recombinant product is extremely high.

BRIEF SUMMARY

Described is a bioactive composition useful for treating damaged and/or injured connective tissues, chronic tendinosis, chronic muscle tears and/or chronic degenerative joint conditions such as osteoarthritis and skin inflammatory disorders. Also described is a method for making the composition. The composition includes an anti-inflammatory component/anti-catabolic component. The anti-inflammatory component is also an anti-catabolic component. For the purposes hereof, the terms "anti-inflammatory component" and "anti-catabolic component" can be used interchangeably. The composition may also include a regenerative component that includes autologous platelet-rich plasma (PRP). Whereas most PRP preparation protocols include an activation step resulting in the immediate release of growth factors and cytokines from platelets, the present disclosure provides a use of a non-activated PRP component for future slow activation of injected composition by surrounding tissue.

The anti-inflammatory/anti-catabolic component preferably comprises IL-1ra, an IL-1 receptor antagonist containing autologous serum. In addition, the anti-inflammatory/anti-catabolic component preferably comprises an increased level of tissue inhibitors of metalloproteinases (TIMPs).

Provided is a method of producing an autologous composition for treating damaged and/or injured connective tissues, chronic tendinosis, chronic muscle tears and/or chronic degenerative joint conditions and skin inflammatory disorders in a mammal comprising the following steps:

A) preparing an anti-inflammatory/anti-catabolic component of the autologous composition comprising TIMPs and IL-1ra, the step of preparing the anti-inflammatory/anti-catabolic component comprising the following steps: i) collecting an autologous physiological fluid, preferably blood from the mammal; ii) delivering the blood to a tube; iii) incubating the blood at a temperature of from about 37° C. to about 39° C. for about 24 hours; iv) centrifuging the blood to separate the blood into a supernatant component and a cellular fraction; and v) collecting the supernatant component;

B) preparing a regenerative component of the autologous composition comprising the following steps: i) collecting blood from the mammal; ii) delivering the blood to a tube in the presence of about 4% sodium citrate; iii) centrifuging the whole blood to separate the platelet-rich plasma component; and iv) collecting the platelet-rich plasma component; and C) mixing the supernatant component of the anti-inflammatory/anti-catabolic component with the platelet-rich plasma component to provide the autologous composition.

For the purposes of the instant disclosure, the terms "sodium citrate" and "citric acid" can be used interchangeably.

Also provided is a method of producing an autologous composition for treating damaged and/or injured connective tissues, chronic tendinosis, chronic muscle tears and/or chronic degenerative joint conditions and skin inflammatory disorders in a mammal comprising the following steps:

A) preparing an anti-inflammatory/anti-catabolic component of the autologous composition comprising TIMPs and IL-1ra, the step of preparing the anti-inflammatory/anti-catabolic component comprising the following steps: i) collecting blood from the mammal; ii) delivering the blood to a tube including sodium citrate; iii) incubating the blood at a temperature of from about 37° C. to about 39° C. for about 24 hours; iv) centrifuging the blood to separate the blood into a supernatant component and a cellular fraction; and v) collecting the supernatant component;

B) preparing a regenerative component of the autologous composition comprising the following steps: i) collecting blood from the mammal; ii) delivering the blood to a tube in the presence of about 4% sodium citrate; iii) centrifuging the whole blood to separate the platelet-rich plasma component; and iv) collecting the platelet-rich plasma component; and C) mixing the supernatant component of the anti-inflammatory/anti-catabolic component with the platelet-rich plasma component to provide the autologous composition.

Further provided is a method of producing an autologous composition for treating damaged and/or injured connective tissues, chronic tendinosis, chronic muscle tears and/or chronic degenerative joint conditions and skin inflammatory disorders in a mammal comprising the following steps:

i) collecting blood from the mammal;
ii) adding sodium citrate to a tube;
iii) delivering the blood to the tube;
iv) incubating the blood at a temperature of from about 37° C. to about 39° C. for about 24 hours;
v) centrifuging the blood to separate the blood into a supernatant component and a cellular fraction; and
vi) collecting the supernatant component.

Further provided is an autologous composition for treating damaged and/or injured connective tissues, chronic tendinosis, chronic muscle tears and/or chronic degenerative joint conditions and skin inflammatory disorders in a mammal produced by the method of the instant disclosure.

Also provided is an autologous composition for treating damaged and/or injured connective tissues, chronic tendinosis, chronic muscle tears and/or chronic degenerative joint conditions and skin inflammatory disorders in a mammal, the composition comprising an anti-inflammatory/anti-catabolic component, preferably including sodium citrate, the anti-inflammatory/anti-catabolic component comprising TIMPs and IL-1ra. The composition further comprises a regenerative component comprising platelet-rich plasma.

Still further provided is an autologous composition for treating damaged and/or injured connective tissues, chronic tendinosis, chronic muscle tears and/or chronic degenerative joint conditions and skin inflammatory disorders in a mammal, the composition comprising an anti-inflammatory/anti-catabolic component, the anti-inflammatory/anti-catabolic component comprising a supernatant component obtained from autologous blood of a mammal, anti-inflammatory/anti-catabolic component including IL-1ra and TIMPs, the composition further comprising a regenerative component comprising platelet-rich plasma obtained from the mammal. The anti-inflammatory/anti-catabolic component preferably includes sodium citrate. Most preferably, the sodium citrate is a 4% solution of sodium citrate.

Also provided is the use of the autologous composition of this disclosure for the treatment of damaged and/or injured connective tissues, chronic tendinosis, chronic muscle tears and/or chronic degenerative joint conditions and skin inflammatory disorders in a mammal.

Further provided is a method of treating a mammal for damaged and/or injured connective tissues, chronic tendinosis, chronic muscle tears and/or chronic degenerative joint conditions and skin inflammatory disorders comprising the following steps:

(i) collecting blood from the mammal;
(ii) delivering the blood to a tube;
(iii) incubating the blood at a temperature of from about 37° C. to about 39° C. for about 24 hours;
(iv) centrifuging the blood to separate the blood into a supernatant component and a cellular fraction;
(v) collecting the supernatant component; and
(vi) preparing a regenerative component of the autologous composition comprising the following steps:
collecting blood from the mammal;
delivering the blood to a tube in the presence of about 4% citric acid;
centrifuging the blood to separate a platelet-rich plasma component from a whole blood;
collecting the platelet-rich plasma component; and
mixing the supernatant component with the platelet-rich plasma component to provide the autologous composition; and
administering the autologous composition to the mammal.

Further provided is a method of treating a mammal for damaged and/or injured connective tissues, chronic tendinosis, chronic muscle tears and/or chronic degenerative joint conditions and skin inflammatory disorders comprising the following steps:

(i) collecting blood from the mammal;
(ii) adding sodium citrate to a tube;
(iii) delivering the blood to the tube;
(iv) incubating the blood at a temperature of from about 37° C. to about 39° C. for about 24 hours;
(v) centrifuging the blood to separate the blood into a supernatant component and a cellular fraction;
(vi) collecting the supernatant component; and
(vii) preparing a regenerative component of the autologous composition comprising the following steps:
collecting blood from the mammal;
delivering the blood to a tube in the presence of citric acid;
centrifuging the blood to separate a platelet-rich plasma component from a whole blood;
collecting the platelet-rich plasma component;
mixing the supernatant component with the platelet-rich plasma component to provide the autologous composition; and
administering the autologous composition to the mammal.

Further provided is a method of treating a mammal for damaged and/or injured connective tissues, chronic tendinosis, chronic muscle tears and/or chronic degenerative joint conditions and skin inflammatory disorders comprising the following steps:

(i) collecting blood from the mammal;
(ii) delivering the blood to a tube in the presence of about 4% sodium citrate;

(iii) incubating the blood at a temperature of from about 37° C. to about 39° C. for about 24 hours;
(iv) centrifuging the blood to separate the blood into a supernatant component and a cellular fraction;
(v) collecting the supernatant component; and
(vi) administering the supernatant component to the mammal.

The compositions and methods described herein are suitable for application to humans. They are also suitable for a wide range of veterinary applications including the treatment of horses, dogs and camels.

The instant disclosure provides an alternative product for treating degenerative joint disease in humans and for veterinary applications including horses, dogs and camels that is relatively safe effective, stable, regenerative, and cost effective.

DETAILED DESCRIPTION

Figure 1:
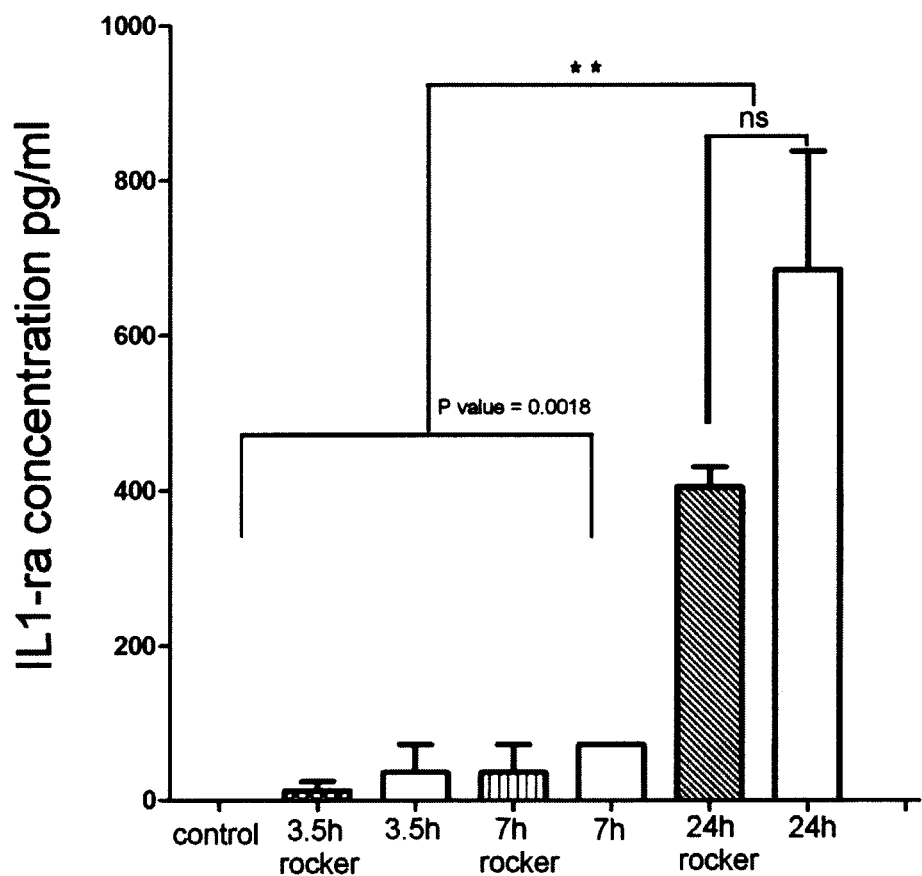
FIG. 1 is a plot of IL-1ra concentration in pg/ml versus time showing a comparison of the level of IL-1ra antagonist protein in human serum samples with varying incubation conditions including stationary and rocking at different time points.

The disclosure relates to a composition comprising an autologous anti-inflammatory/anti-catabolic component and preferably an autologous platelet-rich plasma component with serum enriched by bioactive proteins having a synergistic anti-inflammatory/anti-catabolic, proliferative, tissue remodeling and regenerative effects.

Such a composition typically includes the following therapeutically active proteins: IL-1ra[6], IL-4[7], IL-10[8,9], IL-13[10], PDGF[11], TGF-β[10,11] and VEGF[12,13,14,16].

IL-1ra is secreted by monocytes, adipocytes and epithelial cells. Therapeutically effective concentrations of this protein are achieved by incubating human monocytes at about 37° C. for about 24 hours.[17] IL-4,10,13, PDGF, TGF-β are the content of platelets and-granules and are delivered in the PRP component. IL-4,10,13 come from white blood cells. PDGF is produced by platelets and TGF-B is released by platelets and some T cells. Employing the synergistic effect of the mentioned proteins leads to generation of a potent bioactive autologous product. Thus, a combination of fresh-prepared PRP as a source of regenerative biological factors and anti-inflammatory cytokines and growth factors, and the anti-inflammatory component comprising incubated autologous serum as a source of IL-1 inhibitor provides a powerful and cost-effective autologous therapeutic agent for treatment of degenerative conditions like osteoarthritis, chronic tendinosis and chronic muscle tears as well as skin inflammatory disorders.

As used herein, "treatment" includes palliative treatment, wherein pain and/or inflammation is reduced in the subject.

It is surprising that the method of producing the anti-inflammatory/anti-catabolic component hereof leads to the production of an increased level of tissue inhibitors of metalloproteinases (TIMPs) in addition to the production of IL-1ra. Matrix metalloproteinases MMPs are believed to cause joint destruction when in an active state. TIMPs neutralize active MMPs, thereby providing an additional anti-catabolic benefit that is synergistic with IL-1ra.

It is further surprising that in producing the anti-inflammatory/anti-catabolic component hereof, the addition of sodium citrate prior to incubating a patient's blood at a temperature of from about 37° C. to about 39° C. for about 24 hours, prevents an increased level of pathological molecular agents that have a catabolic effect on joints such as MMP9, IL-1β and TNF-α, but yet does not lead to a significantly decreased level of anti-catabolic and regenerative agents such as TIMPs, IL-1ra and PDGF.

The described method for producing an autologous composition for the treatment of osteoarthritis, chronic tendinosis and chronic muscle tear as well as skin inflammatory disorders preferably comprises the step of collecting a mammal's autologous physiological fluid, preferably blood by an aseptic technique. Preferably, the mammal is a human. However, the compositions and methods hereof are also suitable for a wide range of veterinary applications, for example, for the treatment of horses, dogs and camels.

The site of venipuncture and the surface of the collection tubes may be cleaned with a 2 percent tincture of iodine solution. Before any cleansing of the site is begun, the patient may be asked about any allergy to iodine. The tube covers are also cleaned with 70% alcohol solution to avoid possible contamination before blood collection.

The composition is preferably prepared by culturing autologous physiological fluid, preferably blood, at a temperature from about 37° C. to about 39° C. However, a person skilled in the art will appreciate that the blood can be incubated at temperatures outside this range, for example, from about 37° C. to about 40° C. with acceptable results. Most preferably, the temperature is between 37° C. and 38° C. The blood is incubated for about 24 hours for IL-1ra extracellular enrichment and preferably for the production of TIMPs. Preferably, sodium citrate, preferably at a concentration of 4%, is added to a sterile glass tube or a polystyrene tube into which the blood is collected prior to incubation. In a particularly preferred embodiment, the incubation can be in sterile glass tubes (Coviden) or polystyrene (BD) vacutainer tubes with no additives. Further provided in an embodiment is the incubation of an autologous physiological fluid, preferably blood, on a rocker platform (24 rpm) or in static conditions. Preferably, incubation is carried out in static conditions as shown in FIG. 1.

Figure 2:
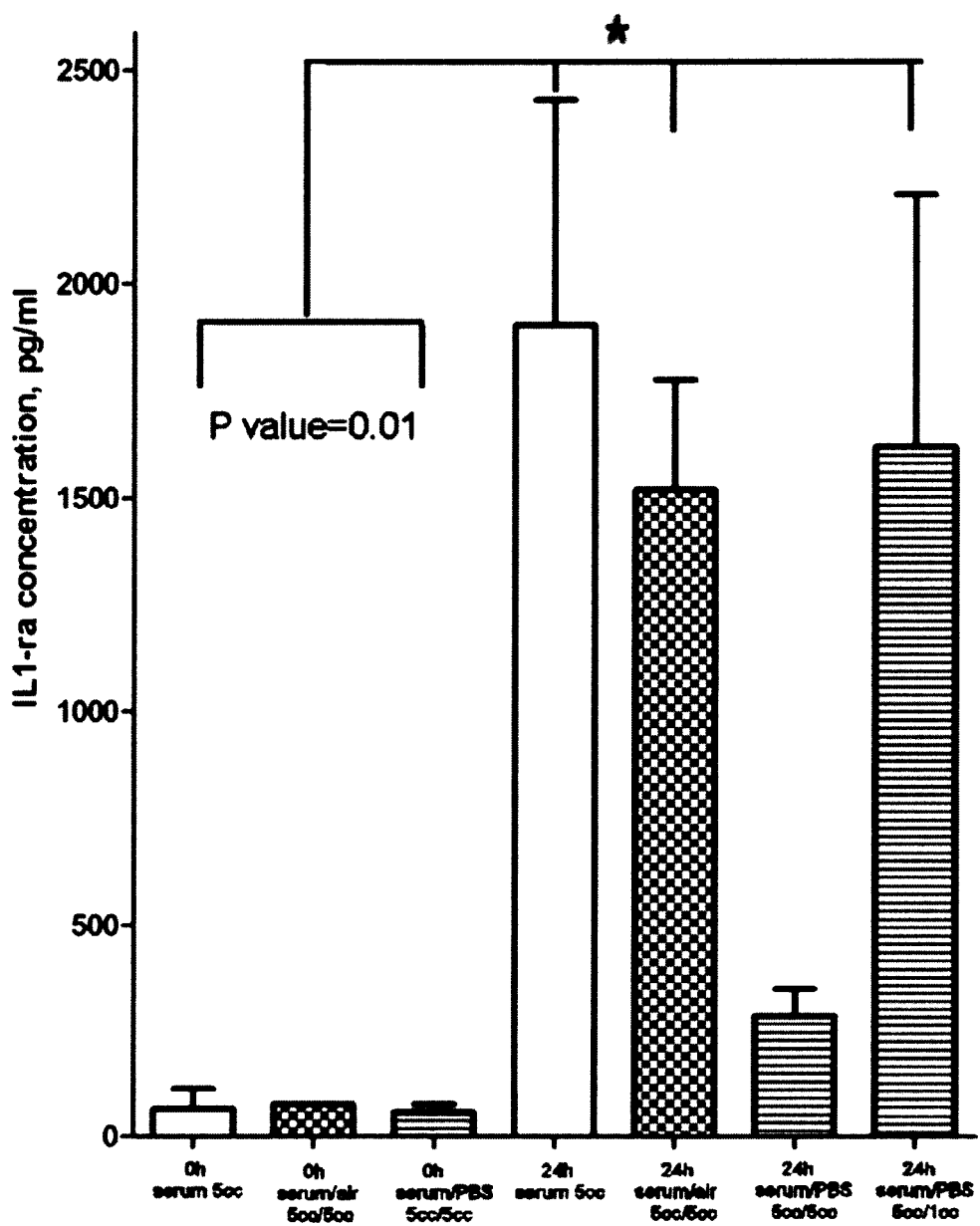
FIG. 2 is a plot of IL-1ra concentration in pg/ml versus time showing a comparison of the level of IL-1ra antagonist protein in the human serum samples at different time points in the presence of air, $Ca^{++}$ (in Phosphate Buffered Saline, PBS) and different concentration of serum.

Preferably, the incubation of blood is in the presence of 0.64-0.72 mM $Ca^{++}$ to facilitate IL-1ra production.[15] It is possible and advantageous in a particularly preferred embodiment to dilute incubated blood with sterile calcium chloride solution containing 0.64-0.72 mM $Ca^{++}$ in 9:1 proportion by adding the solution using a sterile syringe and needle directly to the tube with blood before the incubation (1 cc of the calcium chloride solution to 9 cc whole blood) (FIG. 2). An equal part of sterile air may be added to the sterile tubes containing the blood to expose the blood to atmospheric air for increasing IL-1ra production (FIG. 2). In a particularly preferred embodiment, the air will be passed through a 0.22 μm MILLEX® GP filter using a sterile syringe and needle directly to the tube with the blood before the incubation.

Preferably, sodium citrate is added to the blood prior to incubation in a ratio of 9.5 parts of whole blood (9.5 cc):0.5 (0.5 cc) of preferably 4% sodium citrate. The 4% citrate is preferably a 4% sodium citrate solution. Four percent sodium citrate solutions are readily commercially available.

The incubated blood is then subjected to centrifugation to separate the supernatant component from the cellular fraction. The centrifugation is carried out for about 10-20 minutes at about 4000-10000 rpm. Preferably, the centrifugation is carried out for 10 minutes at 4000 rpm.

The next step involves aspirating the supernatant and dividing it into aliquots for future processing using a sterile technique. The procedure is carried out in a sterile environment (laminar flow hood with HEPA filters). Three cc of the supernatant layer containing biologically active agents are carefully drawn by sterile syringe and needle. Prolonged storage of IL-1ra containing product is accomplished by freezing aliquots at about −20° C. and storing for up to 6 months or up to one year at about −70° C.

The preparation of the regenerative component comprising PRP then involves drawing blood into vacutainer tubes. This is preferably carried out in the presence of 4% citric acid. Preferably, in 9.5 parts of whole blood (9.5 cc): 0.5 (0.5 cc) of 4% citric acid ratio. The blood is then subjected to centrifugation, preferably for about 30 seconds, at about 7500 rpm to isolate the PRP fraction. The centrifugation parameters are used in preferred embodiments for the PRP preparation as a part of the final product for the osteoarthritis and chronic tendinosis treatment and skin disorders. The PRP fraction is drawn by a sterile syringe and needle under sterile conditions. In a particularly preferred embodiment for the treatment of chronic tear, a leukocyte buffy coat fraction is added to the PRP as an additional VEGF source in order to promote new blood vessel development in the affected site. The buffy coat layer and plasma is collected manually by sterile syringe and needle after whole blood centrifugation as set out above or using a commercially available Harvest SMARTPREP® system. The regenerative component comprising PRP is not subject to freezing or other storage. The autologous composition is to be administered to a patient promptly after mixing the regenerative component with the anti-inflammatory/anti-catabolic component.

The anti-inflammatory/anti-catabolic component comprising IL-1ra and preferably TIMPs containing blood is meted with the regenerative component comprising PRP fraction, preferably in a 1:1 ratio, to obtain the final product.

The product is injected for the future slow activation by tendon-derived collagen[18] and tissue-derived thrombin.

The disclosure is further described with the aid of the following illustrative Examples.

EXAMPLES

Example 1—Comparison of Extracellular IL-1ra Production Upon Different Culture Conditions As graphically shown in FIG. 1, a comparison was carried out of the level of IL-1ra antagonist protein in the human serum samples that were exposed to incubation conditions at different time points including stationary versus rocking incubation. IL-1ra is secreted by the activated blood monocyte, macrophages. Such activation is achieved by contact between blood cells and the internal surfaces of the collection tubes through the use of an agitation process. By increasing the internal surface area exposed to the cellular component, the cell activation process and bioactive molecule secretion can be maximized.

Peripheral blood from ten healthy male and female volunteer donors (21 to 60 years old) was collected by venipuncture under sterile conditions to sterile 10 ml glass tubes. One tube was manipulated according to a standard procedure with no incubation step (control sample). Samples were incubated for 3.5 hours, 7 hours, and 24 hours at 37° C. with and without agitation on a rocker platform (24 rpm). Incubated samples were centrifuged for 10 minutes at 4,000 rpm and then filtered, and the final concentrations of IL-1ra were compared to those of unprocessed control samples (0 hours) according to manufacture protocol (available on the internet at bio-rad.com/webroot/web/pdf/lsr/literature/10014905.pdf). A one-way ANOVA test revealed a significant increase of IL-1ra concentration in the serum after 24 hours of incubation only; no significant IL-1ra concentration increase was observed in 3.5-hour and 7-hour incubated samples. Additionally, no significant difference was observed between stationary and rocking incubation conditions. IL-1ra concentration was evaluated using MAGPIX® LUMINEX® technology.

FIG. 2 shows a comparison of the level of antagonist protein in the human serum samples that were exposed to the following incubation conditions: 24 hours incubation in the presence of air, $Ca^{++}$ (in Phosphate Buffered Saline, PBS) and different concentrations of serum. A one-way ANOVA test revealed a significant increase of IL-1ra production in the serum after 24 hours of incubation upon all mentioned conditions besides culturing in 50% diluted blood.

Example 2—Case Reports of Patients Diagnosed with Osteoarthritis and Chronic Tendinosis and Treated with the Autologous Composition Methods and Materials:

For each patient herein, the anti-inflammatory/anti-catabolic component of the autologous composition comprising IL-1ra and TIMPs was prepared by: collecting blood from the patient; delivering the blood to a tube; incubating the blood at a temperature of from about 37° C. to about 39° C. for about 24 hours; centrifuging the blood to separate the blood into a supernatant component and a cellular fraction; and collecting the supernatant component of the anti-inflammatory component. Likewise, the regenerative component of the autologous composition was prepared by: collecting blood from the patient; delivering the blood to a tube in the presence of about 4% citric acid; centrifuging the blood to separate a platelet-rich plasma component from a whole blood component; collecting the platelet-rich plasma component; and mixing the supernatant component of the anti-inflammatory/anti-catabolic component with the platelet-rich plasma component to provide the autologous composition. The autologous composition was then administered to the patient.

Case 1: S, 61 Years Old.

Diagnosis: The patient reported bilateral insidious onset knee pain, which began a few years prior and which had increased within the preceding 6 months. MRI of the knees showed severe OA of the knees: severe chondrosis of the medial compartment with increased amount of full-thickness cartilage loss involving the right and a femoral condyle in the right knee and full thickness chondral loss involving the posterior aspect of the medial femoral trochlea with underlying edema in the right knee. One year earlier, the patient had a Cortisone injection IA, which provided one month relief. Physical exam: Knees Range of Motion (ROM) was full, all ligaments were normal, small bilateral effusion neurovascular exam was normal. VAS was 60.

Treatment: Bilateral injections of the local autologous composition for the patient into the patient's knees three times, a week apart.

Results: After the first injection bilaterally of the local autologous composition for the patient, the patient reported significant improvement, VAS was 3. At the time of the third injection, ROM was full, all ligaments were normal, with no joint line pain, and no effusion. The patient reported strong pain reduction, VAS was 10, the patient went back to physical activity. Three months later, a follow-up exam showed that the patient was pain free.

Case 2: E, 64 Years Old.

Diagnosis: Active male presented with VAS 60 in the left hip. Pain with daily activities and significant impairments with walking for a long distance. Mill showed mild OA in both hips: bilateral hip joint degeneration and acetabular labral degenerative tearing. Physiotherapy treatment had limited success in terms of pain relief.

Treatment: Ultrasound-guided local autologous composition injection prepared for the patient into left hip ×2, a week apart.

Results: After first injection of the local autologous composition, the patient reported an 85% improvement in pain (patient personal assessment). After second injection of the local autologous composition, the VAS was 10. Five months later VAS was also 10.

Case 3: A, 70 Years Old.

Diagnosis: A female patient presented with chronic pain (VAS was 6) tenderness and swelling in the left knee. She had much difficulty in walking, standing, and climbing stairs. She had been to a physical therapist (6 visits), a chiropractor (6 visits) for help with her knee pain with no results. Mill showed severe OA in left knee, with narrowing of the medial compartment due to full-thickness cartilage loss in the weight-bearing portion of the medial femoral condyle and medial tibial plateau.

Treatment: Local autologous composition was made and injections were made into left knee three times, a week apart.

Results: Five-month follow-up visit after treatment with the local autologous composition: the patient reported about 80% improvement in symptoms, no swelling; VAS is 20.

Case 4: J, 26 Years Old, Professional Swimmer.

Diagnosis: Status post paraspinal muscle injury, chronic paraspinal tendonitis. Patient complained of pain over the paraspinal muscle. Prolonged physiotherapy had shown no results. Back ROM is full, neurovascular exam is normal. Area of right paraspinal hyperemia is identified on color Doppler FIG. 3a, VAS was 80.

Treatment: Inflamed area was marked using the ultrasound technique, autologous composition was injected intramuscularly ×4, a week apart.

Figure 3:
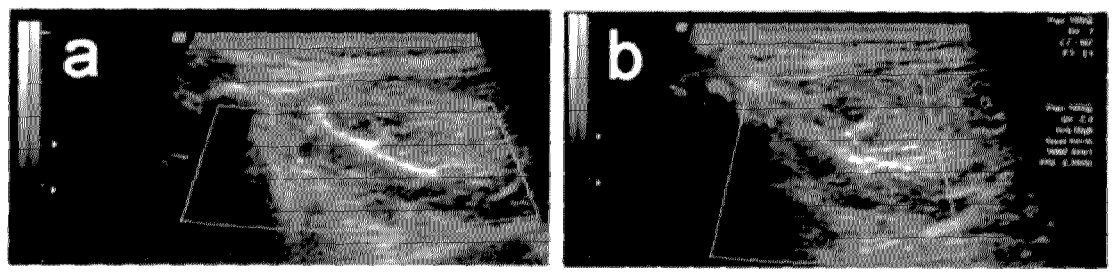
FIGS. 3a and 3b are Doppler ultrasound images of a right paraspinal area of a patient before treatment (FIG. 3a) and normal post-treatment condition (FIG. 3b).

FIGS. 3a and 3b are Doppler ultrasound images that revealed a hyperemia in the right paraspinal area before treatment (FIG. 3a) and normal post-treatment condition (FIG. 3b).

Results: Doppler showed no inflammation (FIG. 3b), VAS was 10 four months after the therapy.

Case 5: S, 18 Years Old.

Figure 4:
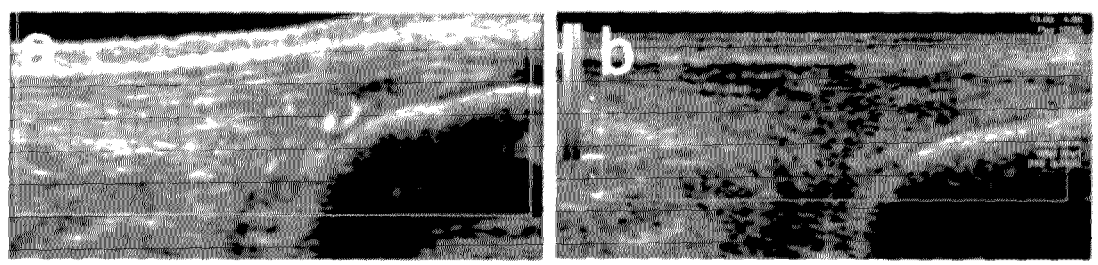
FIGS. 4a and 4b are Doppler ultrasound images showing chronic Achilles tendinosis characterized by excessive hyperemia (FIG. 4a, pre-treatment status), that was resolved as a result of autologous composition treatment (FIG. 4b, post-treatment imaging).

Diagnosis: Status post right Achilles tear. The patient complained of pain in the Achilles insertion: chronic Achilles tendonitis and tenosynovitis. Doppler showed severe intra-tendon hyperemia in the area (FIG. 4a). VAS was 60.

Treatment: Prolonged physiotherapy and chiropractic treatment did not reveal any positive result. Autologous composition was prepared and injected into the tendon three times, a week apart, utilizing ultrasound guidance.

FIGS. 4a and 4b are Doppler ultrasound images that showed chronic Achilles tendinosis characterized by excessive hyperemia (FIG. 4a, pre-treatment status), that was resolved as a result of autologous composition treatment (FIG. 4b, post-treatment imaging).

Results: no hyperemia displayed on Doppler imaging (FIG. 4b), VAS was 0 at five months post-injection follow-up assessment.

Example 3—In Vitro Studies

Peripheral blood from healthy male and female volunteer donors (21 to 60 years old) was collected by venipuncture under sterile conditions to sterile 10 ml glass tubes. One tube was manipulated according to a standard procedure with no incubation step (control sample). Samples were exposed to different incubation conditions and 500 µl of serum from each sample was used for an assay. Samples were centrifuged at 10,000×g for 10 minutes at 4° C. prior to analysis to remove cell debris and aggregates. BioPlex Pro™ Human Cytokine 27-plex Panel, Human TIMP Magnetic LUMINEX® Performance Assay 4-plex Panel™ (Bio-Rad Laboratories, Canada, LTD) analysis with MAGPLEX® beads was performed in a flat-bottom microtiter plate according to the manufacturer's instructions (available on the internet at bio-rad.com/webroot/web/pdf/lsr/literature/10014905.pdf).

Briefly, samples were diluted 1:4 in sample diluent. Standard was reconstituted and diluted in a four-fold dilution series. Antibody-coupled capture beads were prepared and plated. The bead solution was vortexed before addition to each well. The plate was washed, and all wash steps were performed manually. First, the wash solution was added to the plate that was subsequently covered with sealing tape. The plate was incubated on a shaker for 30 seconds at 1100 rpm and then for 1.5 minutes at 300 rpm. The plate was taken off the shaker and was incubated on a magnet for 1 minute before the supernatant was discarded. After washing, diluted samples and standards were added in duplicates to the beads in the wells. The plate was incubated on a shaker for 30 minutes and after incubation and washing, detection antibodies were added for 30 minutes to each well. The plate was again incubated on a shaker and after another washing step, streptavidin solution was added for 10 minutes to the wells. After a last incubation step, the beads were re-suspended in assay buffer and the plate was read with a MAGPIX® (Luminex Corporation) using the xPONENT® software (Luminex Corporation, Austin, Tex., USA). The results were analyzed using the xPONENT® software. The absolute concentrations of the samples were determined by the construction of a standard curve for each analyte.

Statistical analysis: All statistical tests were performed using GRAPHPAD PRISM® version 5.01. Statistical comparisons were performed using analyses of variance (ANOVA) with Bonferroni post-test tests for comparisons between groups. The number of analyzed experiments was ≥3, and data were shown as mean±s.e.m., $p<0.05$.

Figure 5:
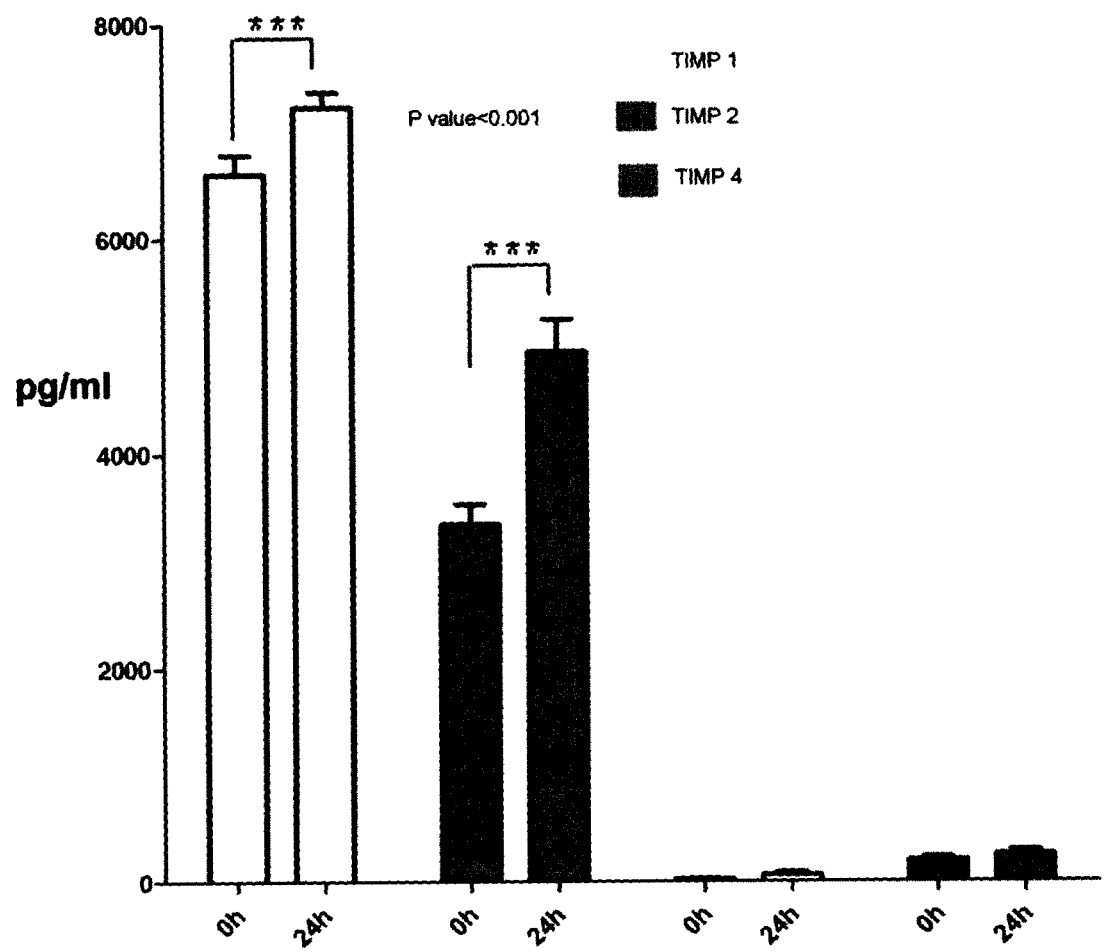
FIG. 5 is a graph showing an average of concentration level of TIMP 1, TIMP 2 and TIMP 4 before and after a 24-hour incubation.

FIG. 5 is a graph showing a comparison of the level of TIMP 1, TIMP 2 and TIMP 4 (MMPS antagonists) proteins in the human serum samples before (baseline level) and after incubation at 37° C. for 24 hours. A two-way ANOVA test revealed a statistically significant increase in the levels of TIMP 1 and TIMP 2 at 24 hours post incubation.

Figure 9:
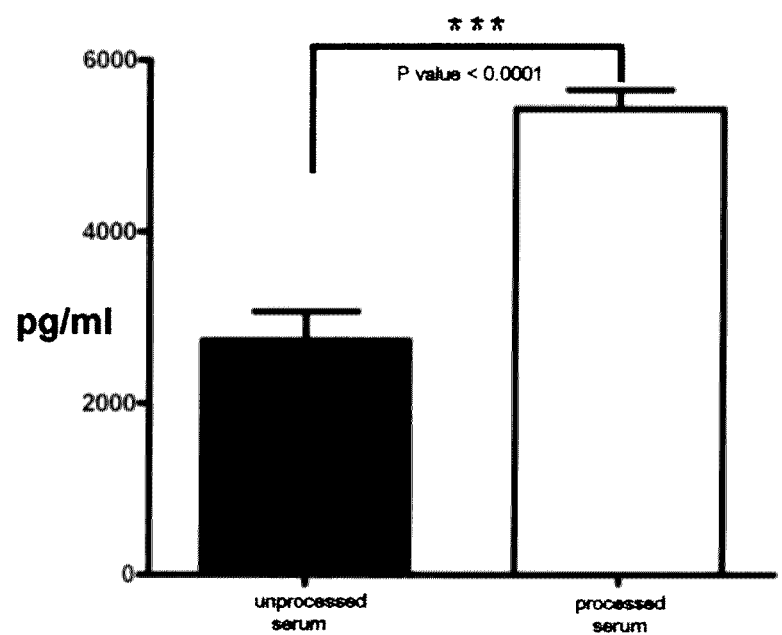
FIG. 9 is graph showing a comparison between the average concentration level of platelet-derived growth factor ("PDGF") in the human serum samples before and after a 24-hour incubation.

FIG. 9 is a graph showing a comparison between the average concentration level of PDGF in the unprocessed human serum samples and an average level of PDGF in 24-hour-incubated samples. Test data analysis showed a statistically significant increase of PDGF protein concentration in processed samples. PDGF concentration was evaluated using MAGPIX® LUMINEX® technology.

Example 4—Results from Patients Treated for Knee Osteoarthritis Joint Pain

Eight patients were treated for symptoms of knee osteoarthritis joint pain. The patients were provided with four injections of the local autologous composition, according to the procedure summarized in Example 2, one week apart.

The patients were assessed after receiving the injections, with Visual Analog Pain Scale (VAS) and the Western Ontario and McMaster Universities Arthritis Index (WOMAC) questionnaire for assessing pain, stiffness, and physical function in patients with hip and/or knee osteoarthritis. The analysis of the WOMAC questionnaire data showed a statistically significant improvement in the patient's daily activities and a statistically insignificant but positive dynamic of improvement in pain and stiffness parameters for the prolonged period (up to 3 months) as shown in FIG. 7. A statistical analysis of the Visual Analog Pain Scale revealed a significant pain reduction after the third injection as shown in FIG. 6.

Figure 6:
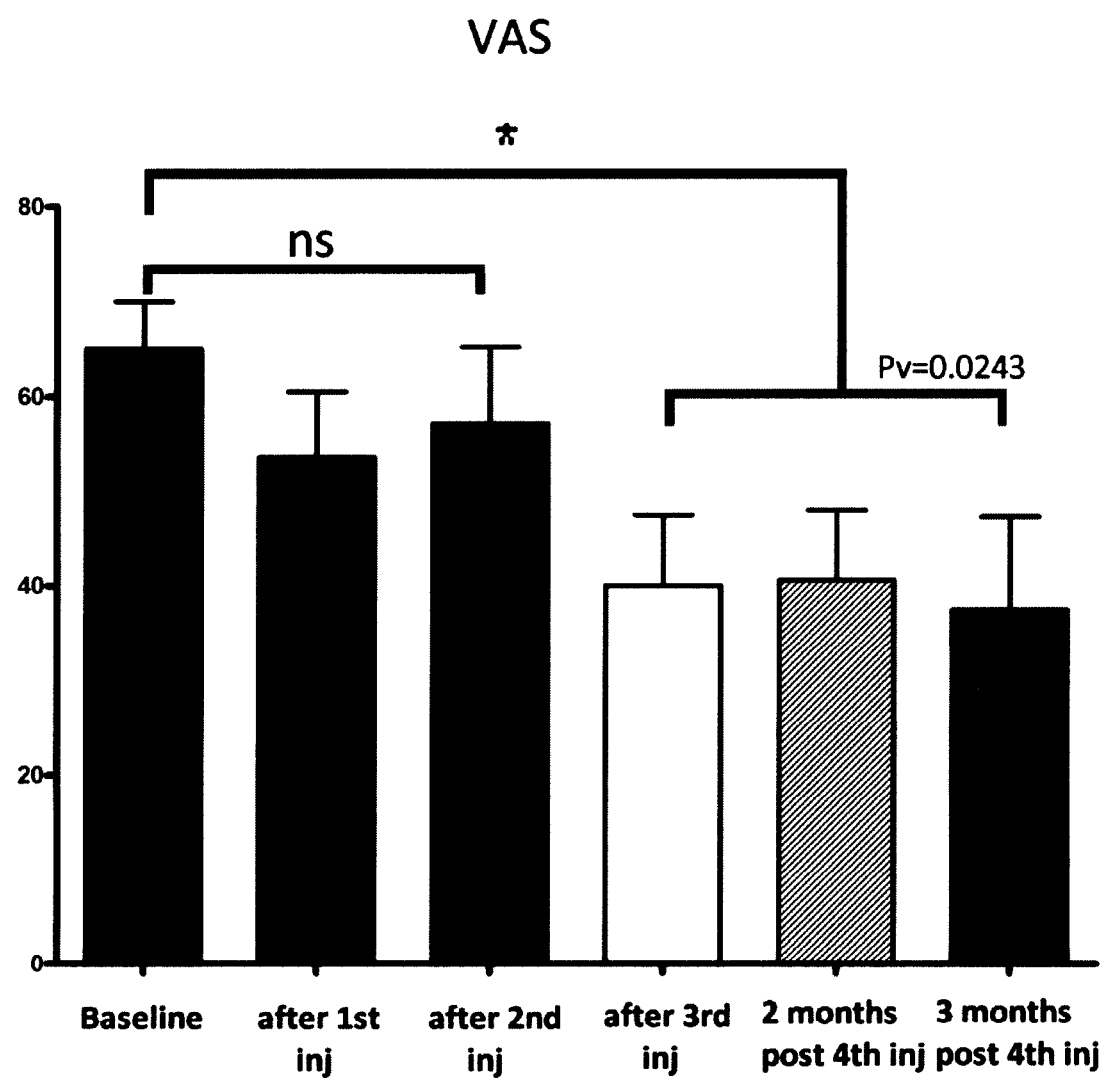
FIG. 6 is a graph showing an average baseline of knee joint pain according to the Visual Analog Scale ("VAS") scale in the eight patients prior to and after injections.
Figure 7:
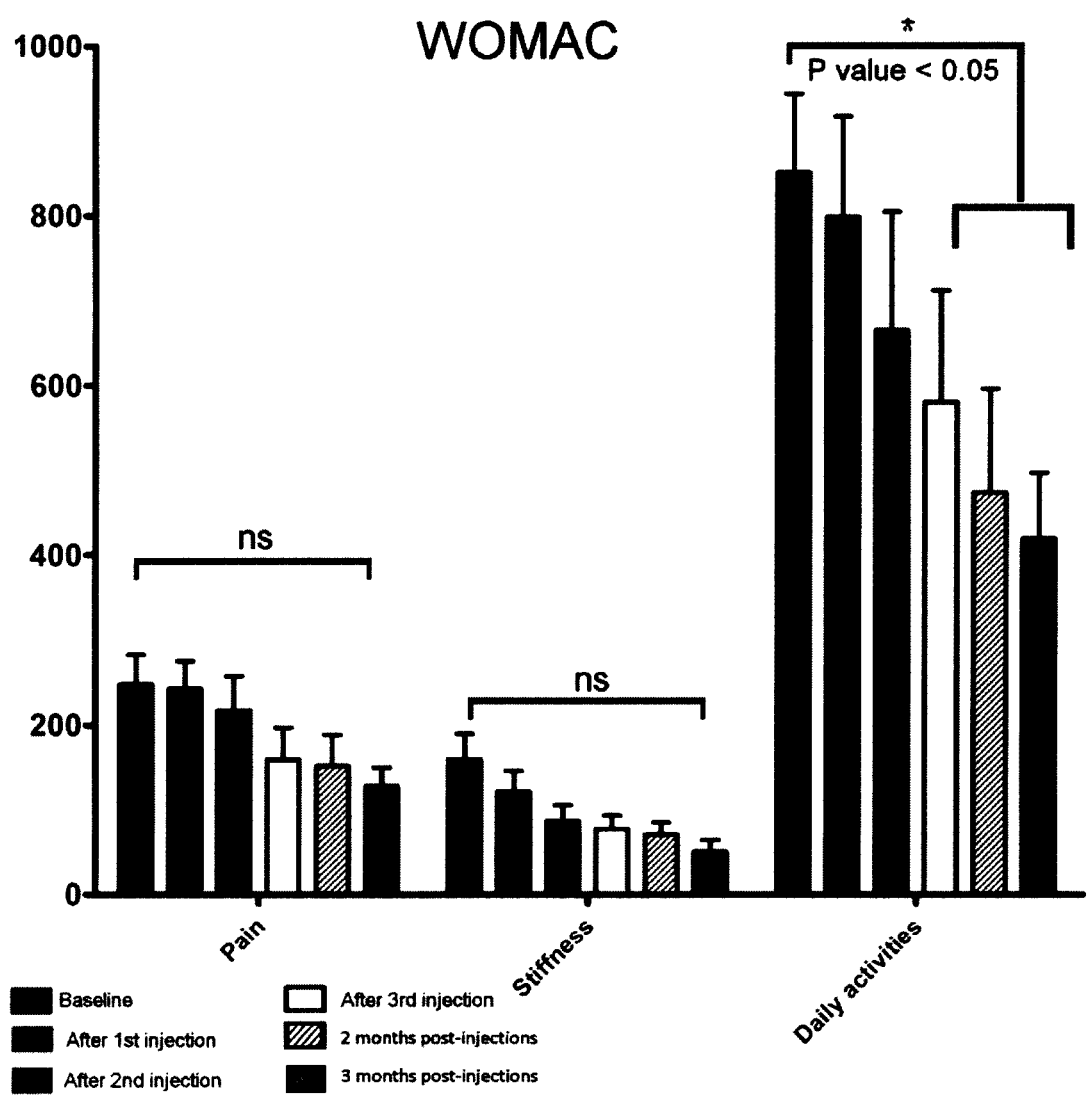
FIG. 7 is a plot showing point values according to the WOMAC index for average levels of knee pain, stiffness and daily activity capabilities among the eight patients.

FIG. 6 is a bar graph showing comparison of an average baseline and post injections of joint pain according to the VAS scale in eight patients. The results show a statistically significant average decrease in pain with stable effect up to 3 months.

FIG. 7 is a plot showing point values according to the WOMAC index for average levels of pain, stiffness and daily activity capabilities among the eight patients. Values are provided for a baseline, after injections, two months and three months post injections.

Figure 8:
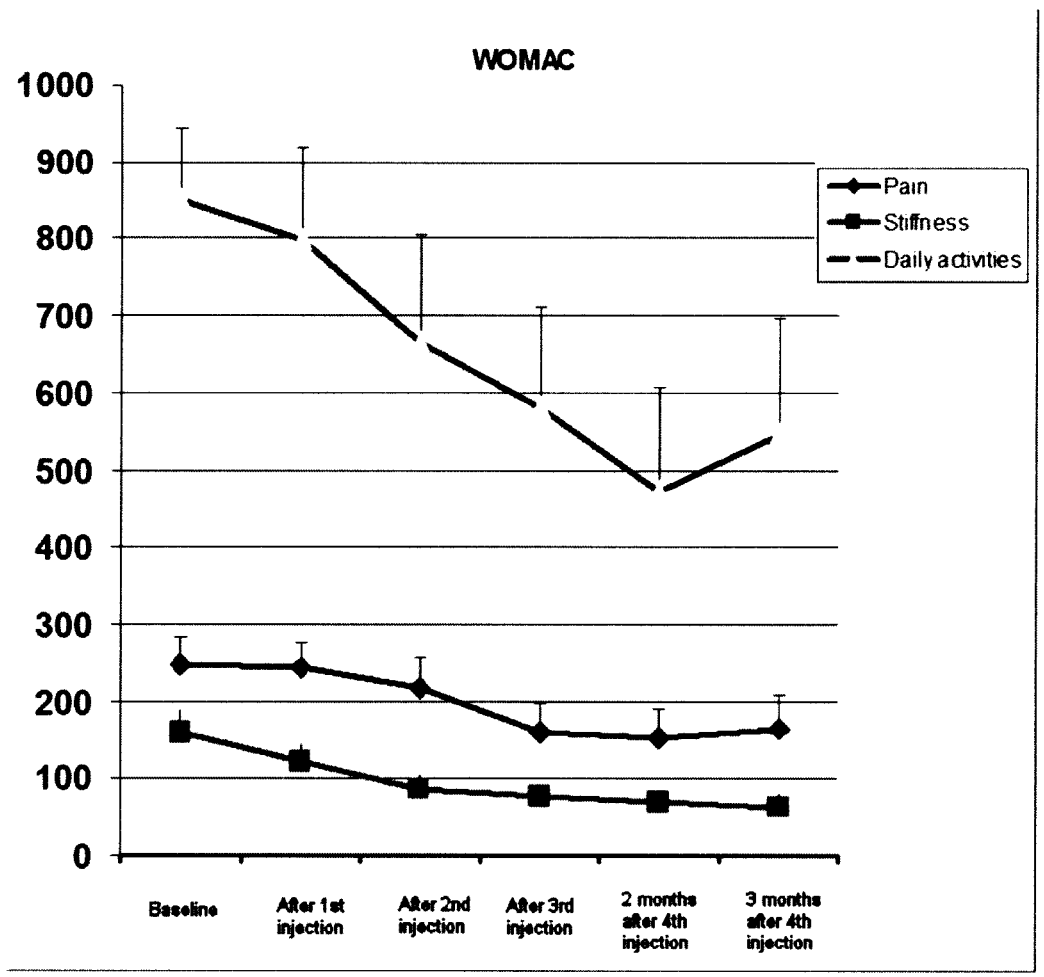
FIG. 8 shows results in the form of a graph providing a breakdown of the average results after the first, second and third injections and two- and three-month follow-ups.

FIG. 8 shows results in the form of a graph among the eight patients providing a breakdown of the average results after the first, second, third injections, two months and three months post the fourth injection.

The results shown in FIGS. 6-8 are average results among the eight patients tested.

Example 5—Effect of Addition of Sodium Citrate (CA) Prior to Incubation in Preparation of Anti-Inflammatory/Anti-Catabolic Component Fifteen patients were tested to determine the effect of the addition of sodium citrate (CA) to the patient's blood, prior to incubation of the blood for about 24 hours, on levels of MMPs including MMP9, IL-1β, TNF-α, TIMP2, Il-1ra, and PDGF in the anti-inflammatory component and in the final product being the combination of the anti-inflammatory component and the regenerative or PRP component.

The terms "blood" and "serum" are used interchangeably in the following discussion.

Methods and Materials:

For each patient herein, an anti-inflammatory/anti-catabolic component was prepared as follows. About 9.5 cc of blood was collected from the patient. The about 9.5 cc of blood was then delivered to a first tube containing about 0.5 cc of saline solution. The saline solution comprised about 0.9% NaCl. Another about 9.5 cc of blood was collected from the patient and delivered to a second tube containing about 0.5 cc of 4% sodium citrate. After collecting the blood, the first and second tubes were incubated at a temperature of from about 37° C. to about 39° C. for about 24 hours. The first and second tubes were then centrifuged to separate the blood in each tube into a supernatant component and a cellular fraction. The supernatant components of the first and second tubes were collected separately to provide a first anti-inflammatory/anti-catabolic component emanating from the first tube containing saline and a second anti-inflammatory/anti-catabolic component emanating from the second tube containing sodium citrate. For each patient, a regenerative component was prepared by: collecting blood from the patient; delivering the blood to a tube in the presence of about 4% citric acid; and centrifuging the blood to separate a platelet-rich plasma component from a whole blood component. For each patient, a platelet-rich plasma component was collected and mixed with the supernatant component of the first and second tubes, respectively, to provide a first final product emanating from the first tube containing saline and a second final product emanating from the second tube containing sodium citrate.

For each patient, a baseline level of MMP2, MMP3, MMP7, MMP9, MMP13, IL-1β, TNF-α, TIMP2, Il-1ra, and PDGF was measured immediately after drawing the blood. For each of the fifteen patients, a level of MMP9, IL-1β, TNF-α, TIMP2, Il-1ra, and PDGF was measured in the first tube containing saline and the patient's blood about 24 hours after incubation. Similarly, for each of the fifteen patients, a level of MMP9, IL-1β, TNF-α, TIMP2, Il-1ra, and PDGF was measured in the second tube containing sodium citrate and the patient's blood about 24 hours after incubation. For each patient, the platelet-rich plasma component was mixed with thrombin and then the levels of MMP9, IL-1β, TNF-α, TIMP2, Il-1ra, and PDGF were measured. For each patient, a level of MMP9, IL-1β, TNF-α, TIMP2, Il-1ra, and PDGF was measured in each of the first and second final products. The measurements shown graphically in FIGS. 10-17 represent averages of the fifteen patients tested.

In the fifteen patients tested, an average level of IL-1ra in native serum (blood) at 0 hours of incubation was measured to be 9±4 pg/ml. In the final product resulting from the combination of the anti-inflammatory/anti-catabolic component with the regenerative or PRP component, the average measurement for IL-1ra in native serum (blood) was 920±80 pg/ml. This was the case, both with the addition of sodium citrate to the anti-inflammatory/anti-catabolic component and where no sodium citrate was added.

In the fifteen patients tested, an average level of PDGF in native serum (blood) at 0 hours of incubation was measured to be 1100±300 pg/ml. In the final product resulting from the combination of the anti-inflammatory/anti-catabolic component with the regenerative or PRP component, the average measurement for PDGF in native serum (blood) was 1920±380 pg/ml. This was the case, both with the addition of sodium citrate to the anti-inflammatory/anti-catabolic component and where no sodium citrate was added.

In the fifteen patients tested, an average level of TIMP2 in native serum (blood) at 0 hours of incubation was measured to be 1800±150 pg/ml. In the final product resulting from the combination of the anti-inflammatory/anti-catabolic component with the regenerative or PRP component, the average measurement for TIMP2 in native serum (blood) was 5500±360 pg/ml. This was the case, both with the addition of sodium citrate to the anti-inflammatory/anti-catabolic component and where no sodium citrate was added.

In these figures, serum 0 hours is the baseline measurement of the level of the analyte in the patients' blood measured immediately upon collection. Serum 24 hours+0.5 cc saline is the level of the analyte in the patients' blood mixed with saline solution after 24 hours of incubation. Serum 24 h+0.5 cc CA is the level of the analyte in the patients' blood mixed with 4% sodium citrate solution after 24 hours of incubation. PRP+Thrombin is the level of the analyte in the PRP component combined with thrombin as a clotting agent. This measurement shows a baseline level of analyte in the PRP component. PRP+Serum+Thrombin or PRP+Serum 24 h+Thrombin is the level of the analyte in the final product resulting from the combination of the anti-inflammatory/anti-catabolic component with the regenerative or PRP component where the anti-inflammatory/anti-catabolic component was prepared with saline only and no sodium citrate. PRP+Serum+CA+Thrombin or PRP+Serum 24 h+CA+Thrombin is the level of the analyte in the final product resulting from the combination of the anti-inflammatory/anti-catabolic component with the regenerative or PRP component where the anti-inflammatory/anti-catabolic component was prepared with sodium citrate.

Figure 10:
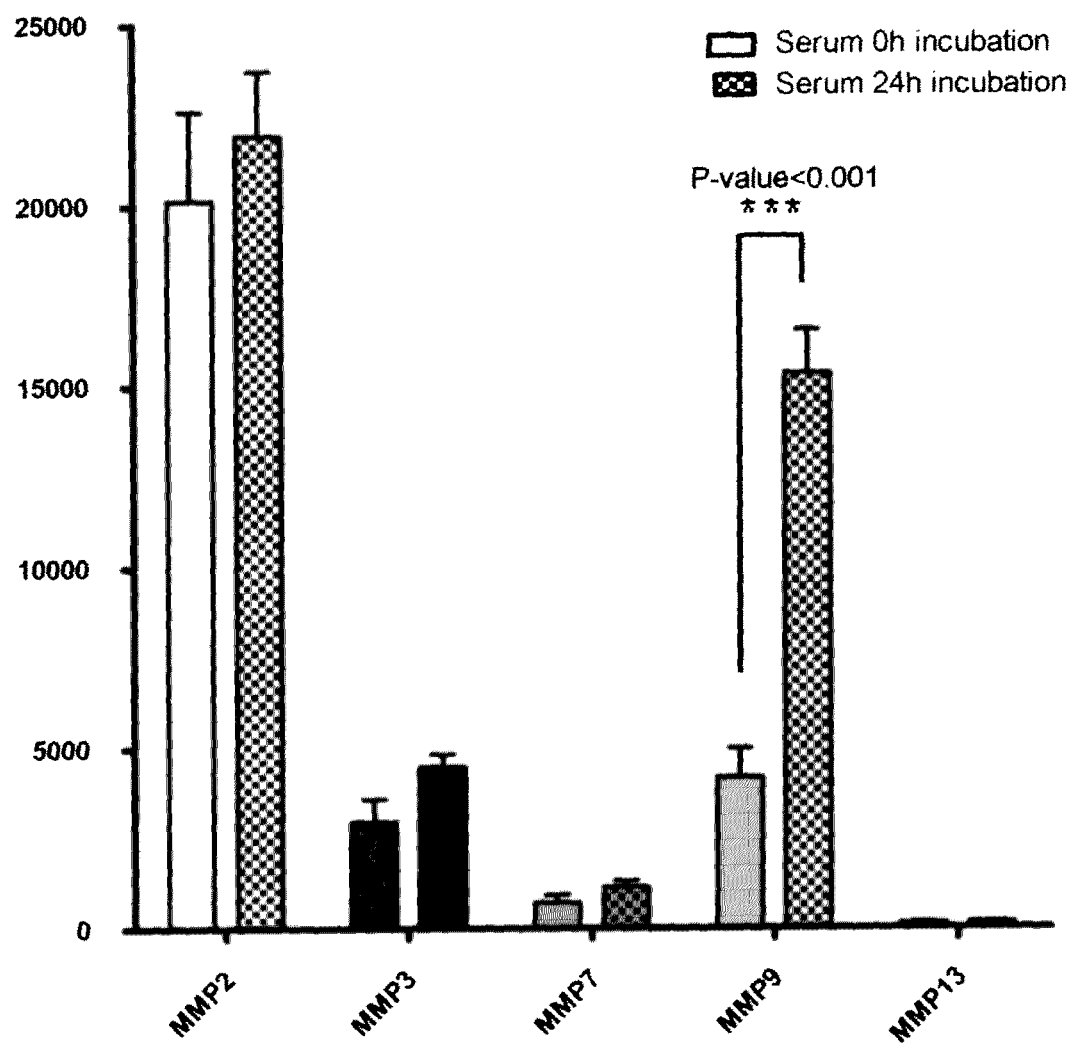
FIG. 10 is a graph showing a comparison of the level of MMP2, MMP3, MMP7, MMP9 and MMP13 proteins in human serum samples before (baseline level) and after incubation at 37° C. for 24 hours.

In preparing the anti-inflammatory/anti-catabolic component as set out in the procedure of Example 2, it was observed that the production of this component results in an increased level of IL-1ra (anti-inflammatory agent), TIMPs (anti-catabolic agents) and PDGF (regenerative agent) after the incubation step. The method of producing the autologous bioactive composition is based on the ability of activated blood mononuclear cells to secrete positive bioactive molecules. However, it has now been determined that the same immune cells un-selectively produce both pathological molecular agents and their inhibitors upon their activation. Thus, the autologous bioactive composition also contains an elevated concentration of catabolic molecules such as MMP9. This was confirmed by quantitative measurement of four MMP types in the anti-catabolic component prepared after incubating the patients' blood in the presence of saline at about 37° C. to about 39° C. for about 24 hours, as shown in FIG. 10. While the concentrations of MMP 2,3,7,13 were not found significantly changed after incubation, the concentration of MMP9, which is most critical for osteoarthritis pathogenesis, was significantly increased, as shown in FIG. 10. A one-way ANOVA test revealed a statistically significant increase in the levels of MMP9 at 24 hours post incubation.

Figure 11:
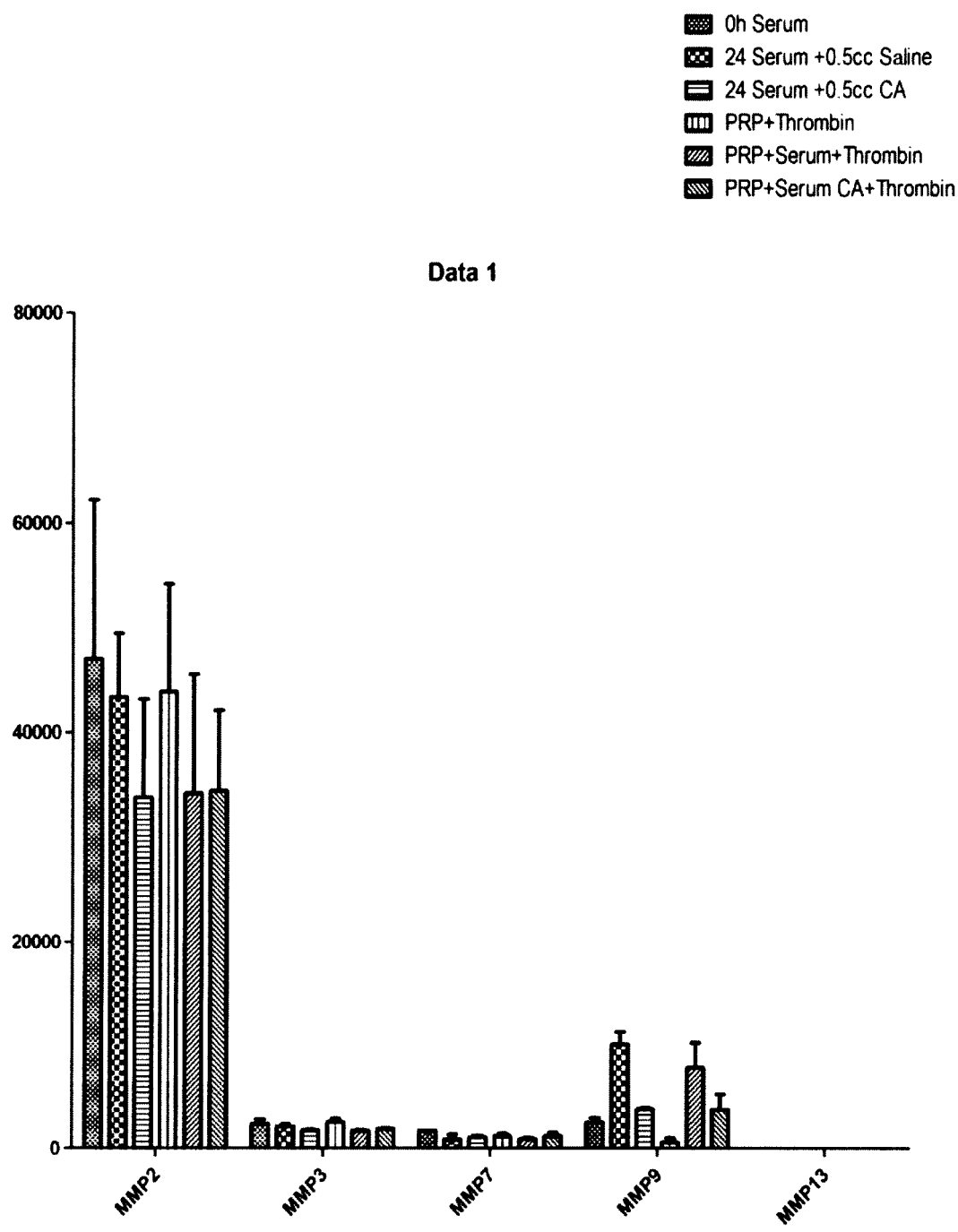
FIG. 11 is a graph showing a comparison of the level of MMP2, MMP3, MMP7, MMP9 and MMP13 proteins in human serum samples before (baseline level) and after incubation at 37° C. for 24 hours in the presence of sodium citrate.
Figure 12:
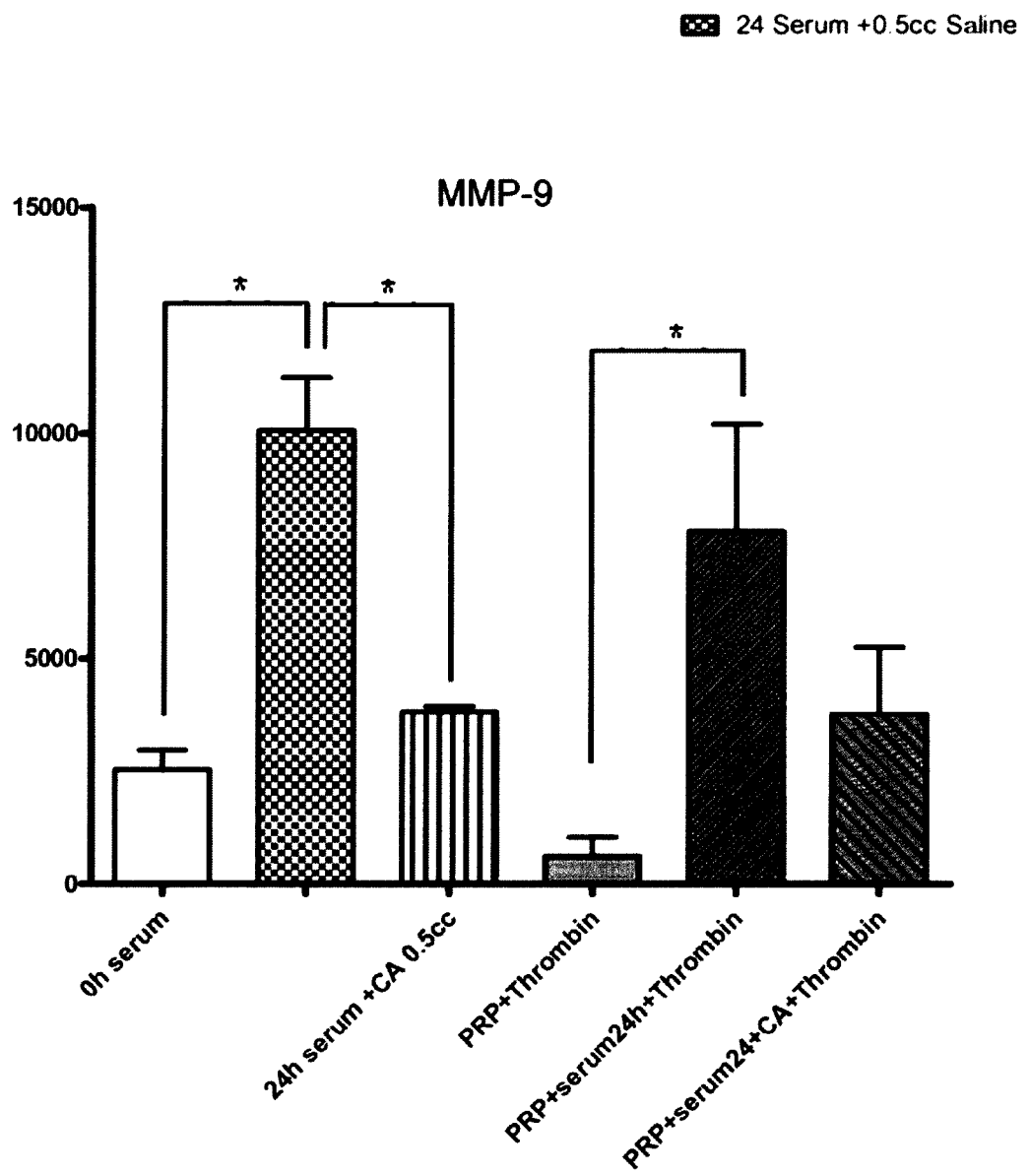
FIG. 12 is a graph showing the MMP9 data from FIG. 11.

The presence of increased MMP9 concentration in the autologous bioactive composition may result in an adverse effect manifestation during the patient treatment process. It is, therefore, desired to selectively eliminate this negative component. The presence of the anticoagulant, sodium citrate, significantly down-regulates MMP9 release by human blood leukocytes.[19] Human blood in the presence of sodium citrate (CA) at a ratio of 9.5 cc blood:0.5 cc sodium citrate was incubated at a temperature of from about 37° C. to about 39° C. for 24 hours and found strong dynamic changes, especially in MMP9 secretion as shown in FIGS. 11 and 12. Particularly, adding sodium citrate in preparing the anti-inflammatory/anti-catabolic component significantly decreased MMP9 concentration in the final product of the combination of the anti-inflammatory/anti-catabolic component and the regenerative component (thrombin-activated PRP+24 h serum). The MMP9 level after a 24-hour incubation did not change compared to the baseline level (0 hours) where sodium citrate was added in preparing the anti-inflammatory/anti-catabolic component. A measurement of the level of MMP9 in PRP component with thrombin was made to show a baseline level of MMP9 in the PRP component. This measurement shows that no significant quantity of MMP9 is produced in generating the PRP component.

Given that the blood incubation process leads to an elevation of the pro-catabolic molecule MMP9, concentrations of other pathological molecular agents, namely IL-1β and TNF-α were tested in incubated serum and in the final product of the combination of the anti-inflammatory/anti-catabolic component and the regenerative component (thrombin-activated PRP+blood serum incubated for 24 hours). The effect of sodium citrate on these molecules released by activated leukocytes during incubation was tested. It was found that although both IL-1β and TNF-α concentrations are significantly increased upon incubation. This effect could be efficiently blocked by adding sodium citrate in preparing the anti-inflammatory/anti-catabolic component, as shown in FIGS. 13 and 14.

Figure 13:
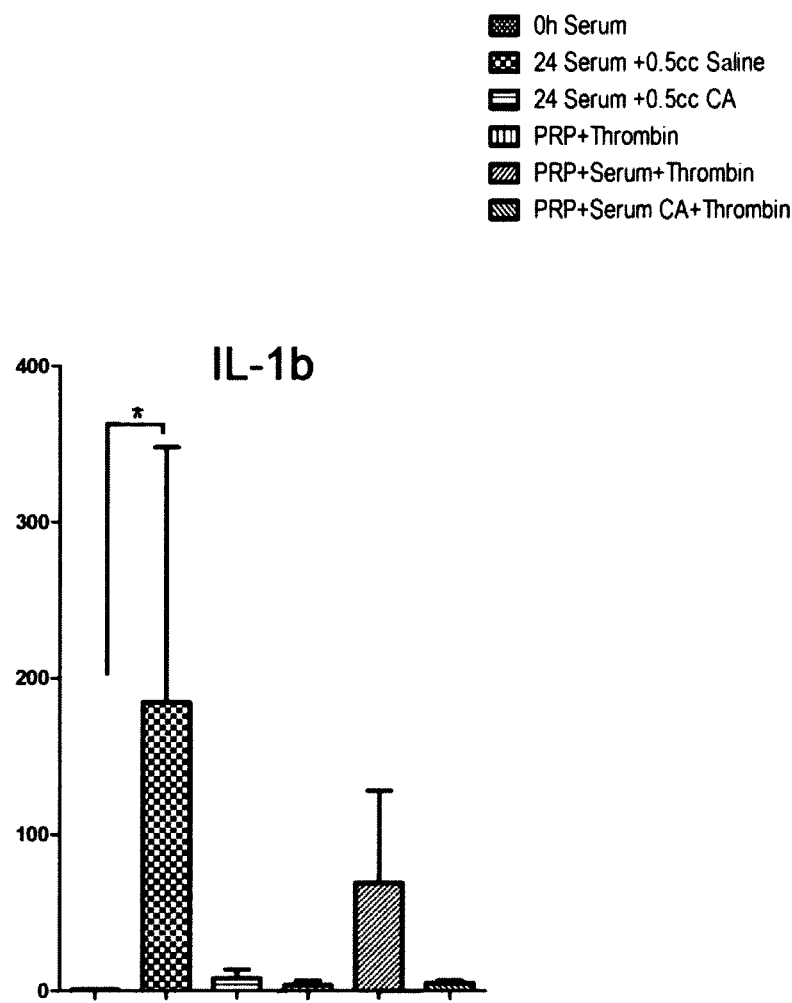
FIG. 13 is graph showing a comparison of the level of IL-1β in human serum samples before (baseline level) and after incubation at 37° C. for 24 hours, activated PRP, and in the final composition.

With reference to FIG. 13, a two-way ANOVA test revealed a statistically significant decrease in IL-10 concentration in 24-hour-incubated blood serum from about 37° C. to about 39° C. in the presence of sodium citrate as well as in the final product (PRP+serum 24 h+sodium citrate (CA)+Thrombin) as compared to the previous method for product preparation (PRP+serum 24 h+saline). As referred to throughout, the final product (PRP+serum 24 h+CA+Thrombin), is the combination of the anti-inflammatory/anti-catabolic component and the regenerative component.

Figure 14:
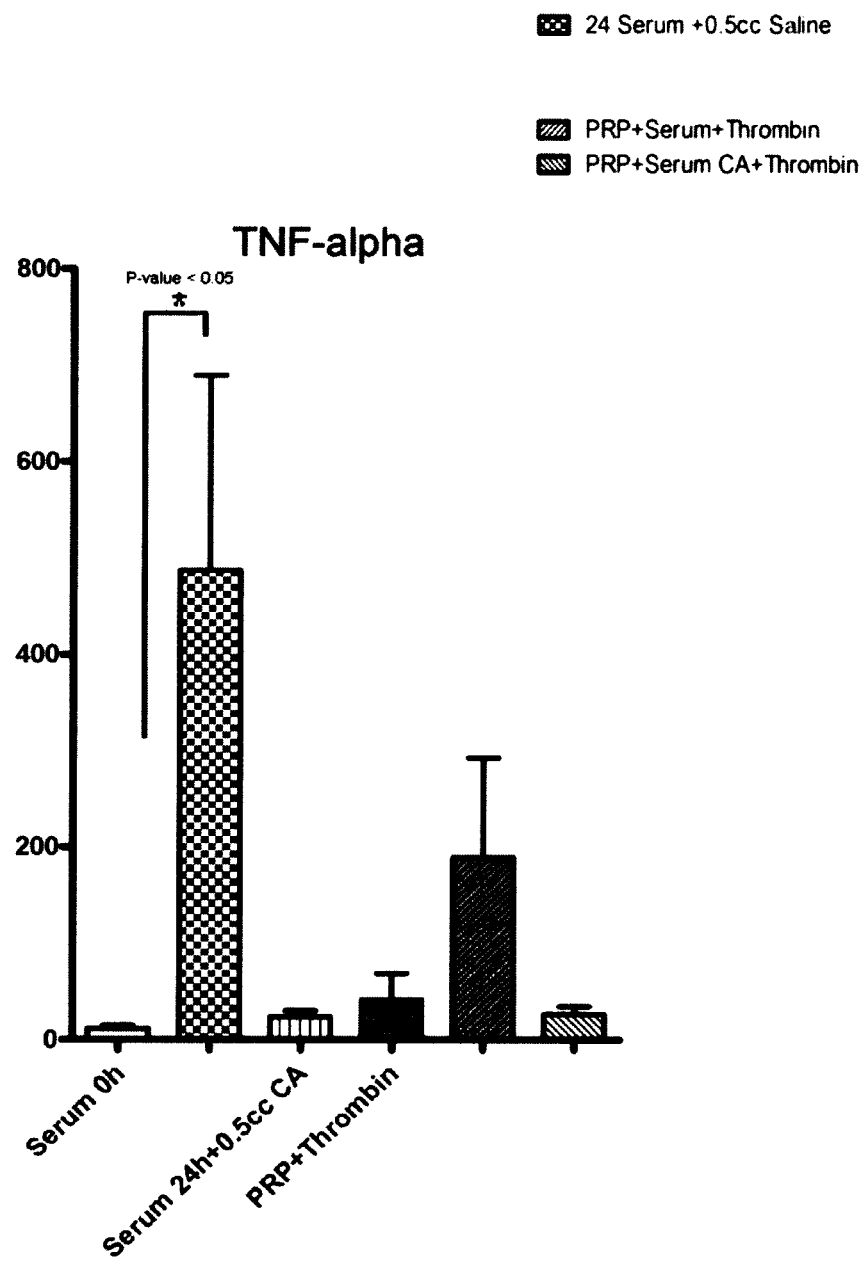
FIG. 14 is a graph showing a comparison of the level of TNF-α in human serum samples before (baseline level) and after incubation at 37° C. for 24 hours, activated PRP, and in the final composition.

With reference to FIG. 14, a two-way ANOVA test revealed a statistically significant decrease of TNF-α concentration in 24-hour-incubated serum from about 37° C. to about 39° C. in the presence of sodium citrate as well as in the final product (PRP+serum 24 h+CA+Thrombin) as compared to the previous method of product preparation (PRP+serum 24 h+saline).

To evaluate whether the addition of sodium citrate to the anti-inflammatory/anti-catabolic component affects pathological molecular agent inhibitors during bioactive composition preparation, TIMPs, Il-1ra and PDGF concentrations were tested upon similar conditions. No negative effects of sodium citrate on TIMPs, Il-1ra and PDGF production were observed as shown in FIGS. 15, 16, and 17.

Figure 15:
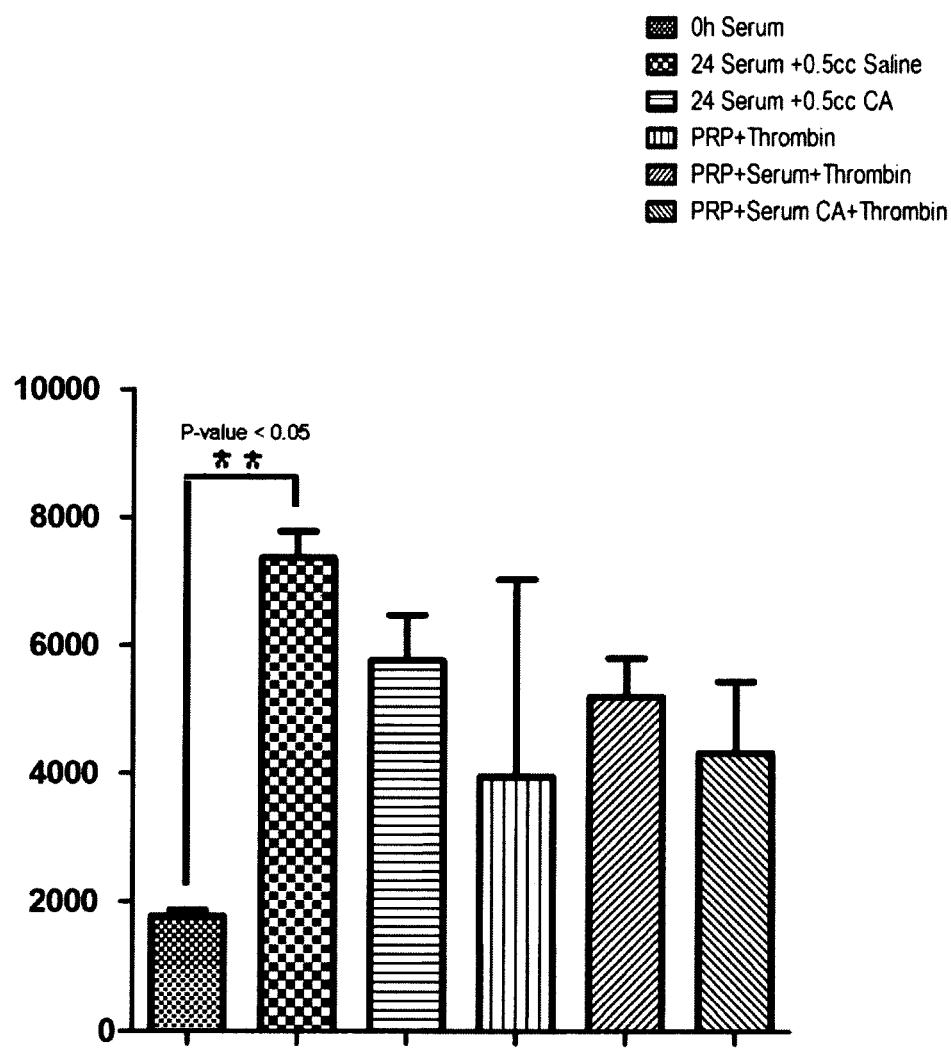
FIG. 15 is a graph showing a comparison of the level of TIMP2 in the human serum samples before (baseline level) and after incubation at 37° C. for 24 hours, activated PRP, and in the final composition.

With reference to FIG. 15, a comparison of the level of TIMP2 in the human serum samples was conducted before (baseline level), after incubation at 37° C. for 24 hours, activated PRP and in the final product. A two-way ANOVA test revealed that sodium citrate does not decrease the concentration of TIMPs in 24-hour-incubated serum in the presence of sodium citrate as well as in the final product (PRP+serum 24 h+CA+Thrombin) as compared to the previous method of product preparation (PRP+serum 24 h+saline).

Figure 16:
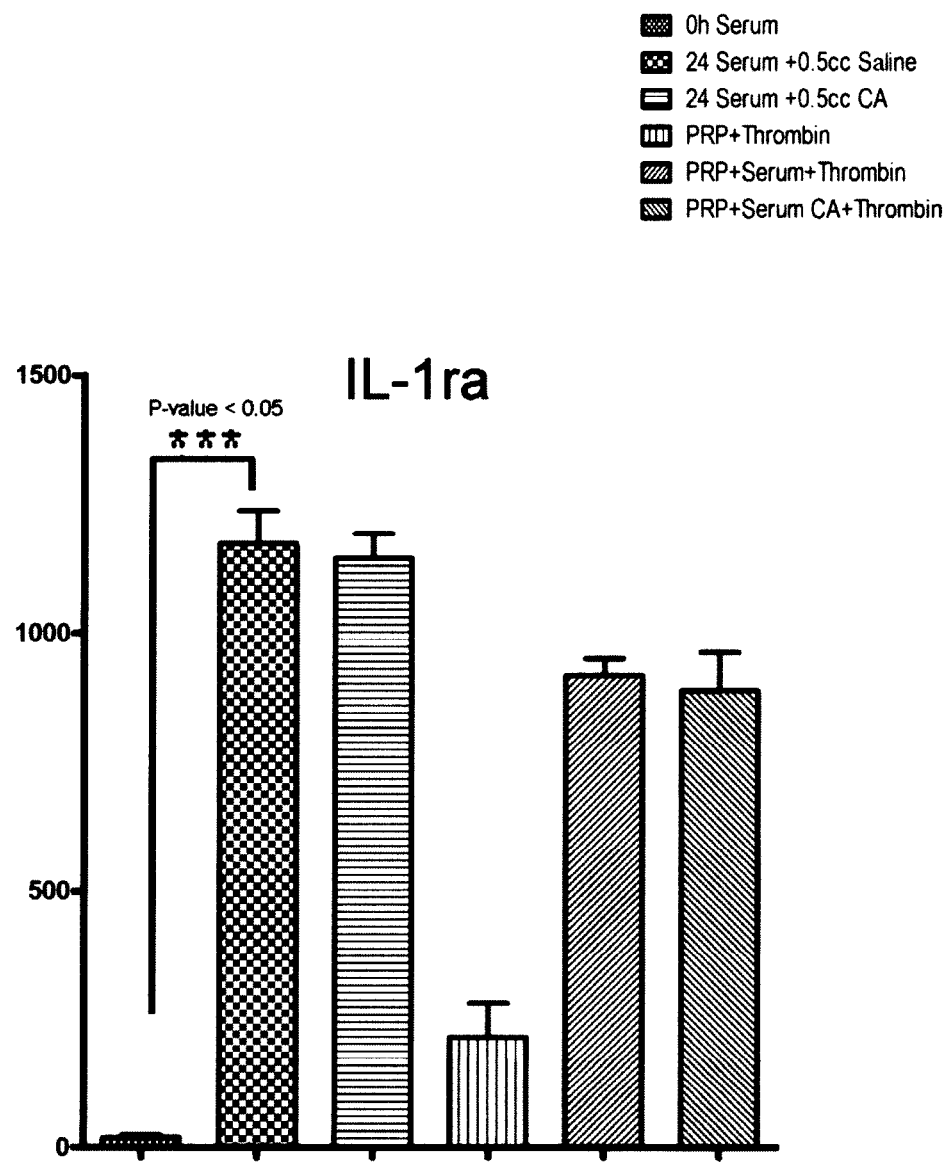
FIG. 16 is a graph showing a comparison of the level of IL-1ra in human serum samples before (baseline level) and after incubation at 37° C. for 24 hours, activated PRP, and in the final product.

With reference to FIG. 16, a two-way ANOVA test revealed that sodium citrate does not decrease IL-1ra concentration in 24-hour-incubated serum in the presence of sodium citrate as well as in the final product (PRP+serum 24 h+CA+Thrombin) as compared to the previous method of product preparation (PRP+serum 24 h+saline).

Figure 17:
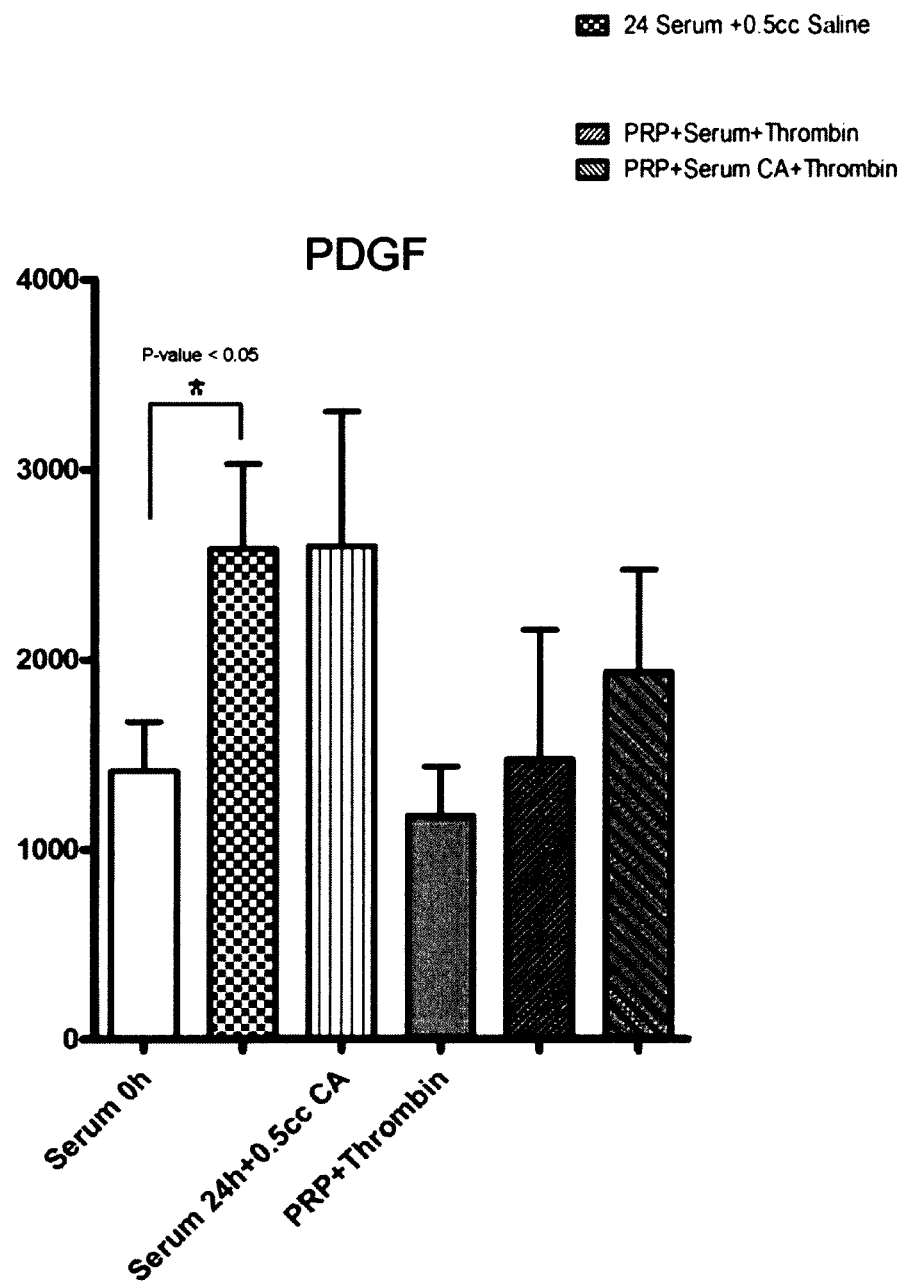
FIG. 17 is a graph showing a comparison of the level of PDGF in the human serum samples before (baseline level) and after incubation in 37° C. for 24 hours, activated PRP, and in the final composition.

With reference to FIG. 17, a two-way ANOVA test revealed that sodium citrate does not decrease PDGF concentration in 24-hour-incubated serum as well as in the final product (PRP+serum 24 h+CA+Thrombin) as compared to previous method product preparation (PRP+serum 24 h+saline).

Example 6—Treatment of Patients with Symptoms of Knee Osteoarthritis Joint Pain Seventeen patients were treated for symptoms of knee osteoarthritis joint pain according to the method described herein, as summarized in Example 2. Two groups of patients were provided with two injections one week apart. A first group of seven patients received a product including the anti-inflammatory/anti-catabolic component prepared with no presence of sodium citrate (CA−). A second group of ten patients received a product including the anti-inflammatory/anti-catabolic component prepared with the presence of sodium citrate (CA+). Both treatments did not result in any adverse events and were found to be safe and effective.

Figure 18A:
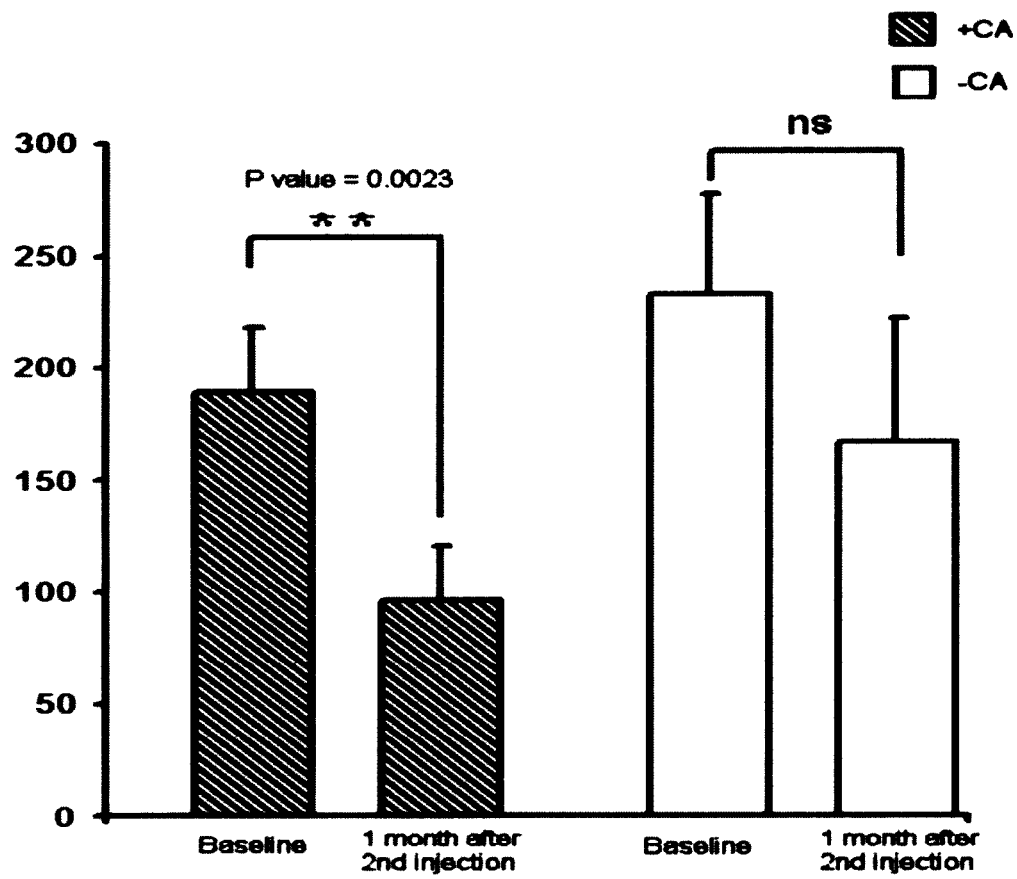
FIG. 18a is a plot showing point values according to the WOMAC index for average levels of pain among seventeen patients tested. Values are provided for a baseline and 1 month post injections for CA− and CA+ groups.
Figure 18B:
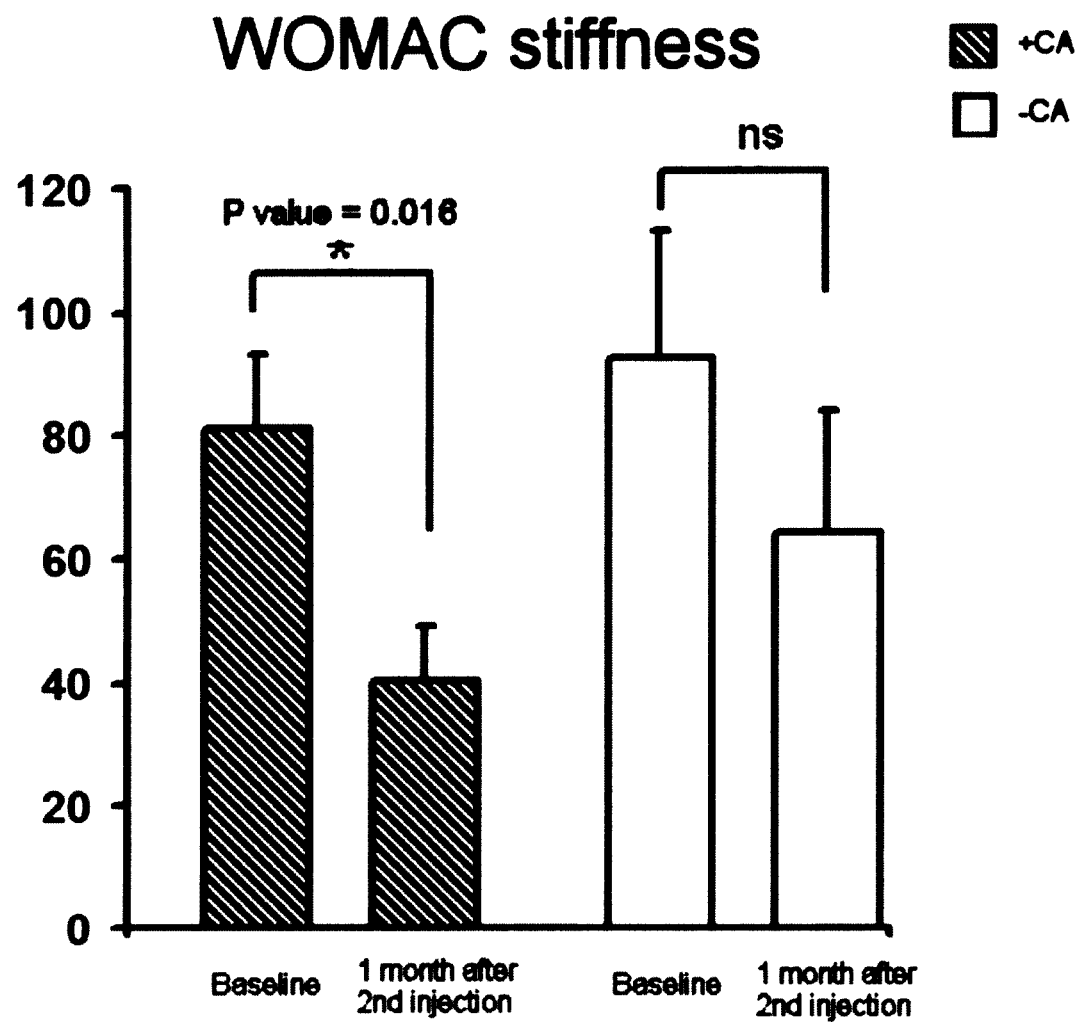
FIG. 18b is a plot showing point values according to the WOMAC index for average levels of stiffness among the seventeen patients tested. Values are provided for a baseline and 1 month post injections for CA− and CA+ groups.
Figure 18C:
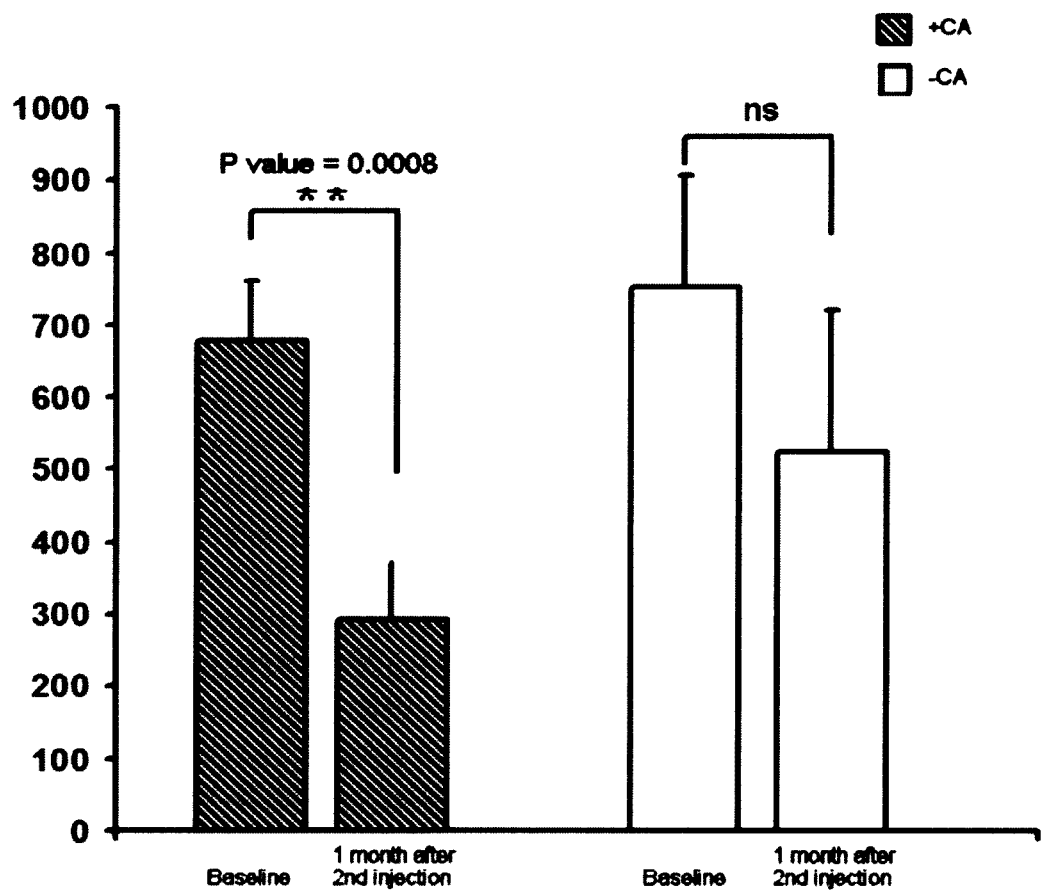
FIG. 18c is a plot showing point values according to the WOMAC index for average levels of daily activity capabilities among the seventeen patients tested. Values are provided for a baseline and 1 month post injections for CA− and CA+ groups.
Figure 18D:
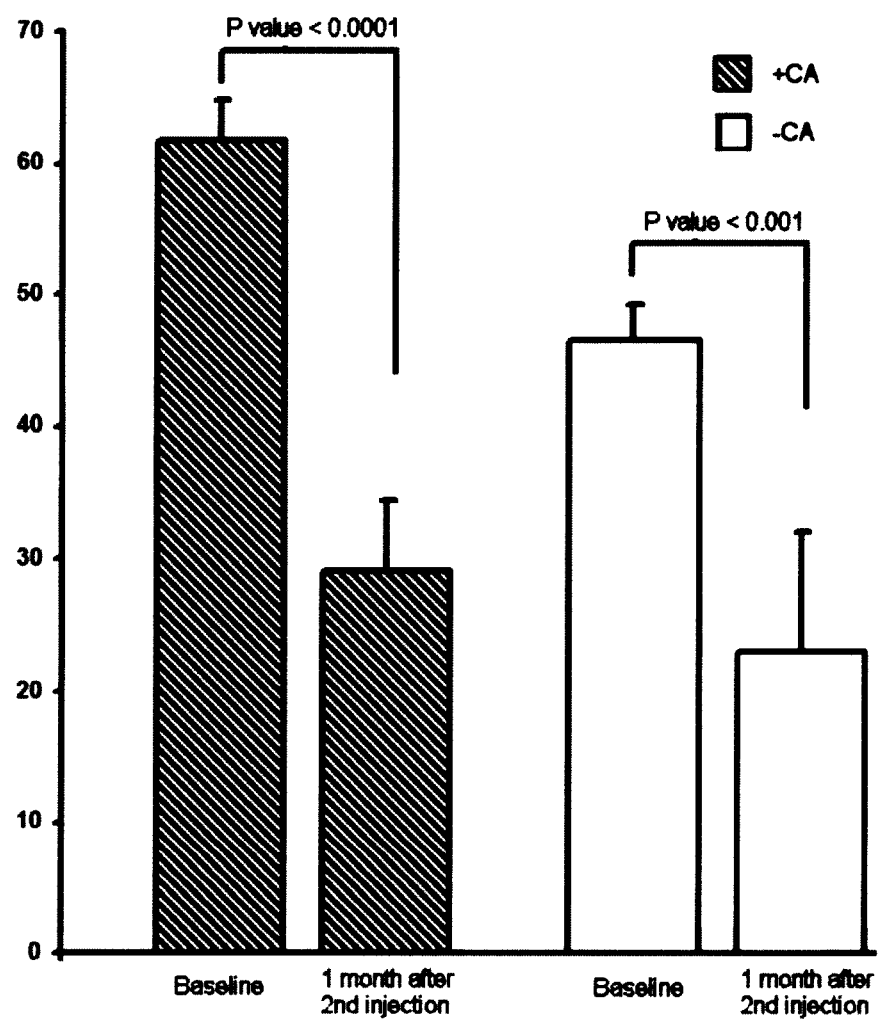
FIG. 18d is a plot showing a statistical analysis of Visual Analog Pain Scale (VAS) among the seventeen patients tested. Values are provided for a baseline and 1 month post injections for CA− and CA+ groups.

The patients were assessed with the Western Ontario and McMaster Universities Arthritis Index (WOMAC) questionnaire for assessing pain, stiffness, and physical function in patients with hip and/or knee osteoarthritis. A one month post-injection preliminary analysis of the WOMAC questionnaire data showed a statistically significant improvement in the patients' pain, stiffness and daily activities in patients treated with the anti-inflammatory/anti-catabolic component having citrate (CA+) as shown in FIGS. 18a, 18b, and 18c, respectively. With the group of patients treated with the anti-inflammatory/anti-catabolic component not having citrate (CA−), a statistically insignificant but positive dynamic of improvement in the mentioned parameters was observed as shown in FIGS. 18a, 18b, and 18c, respectively. A statistical analysis of Visual Analog Pain Scale (VAS) revealed a significant pain reduction in both groups, as shown in FIG. 18d.

Example 7—Chronic Inflammatory Skin Diseases

Figure 19A:
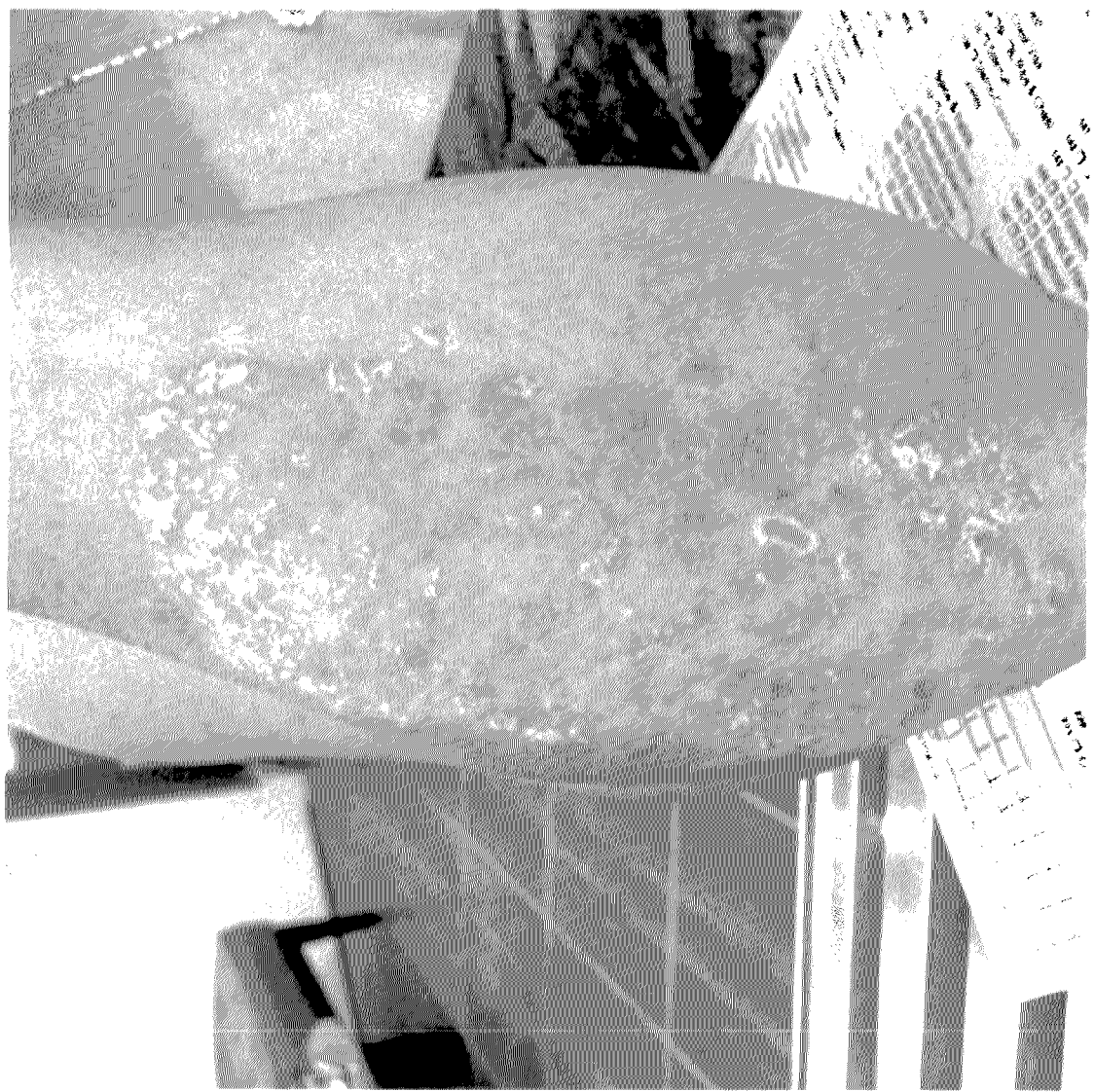
FIG. 19a is a photograph of skin on the arm of a patient suffering from psoriasis prior to treatment with the method of the present disclosure.
Figure 19B:
FIG. 19b is a photograph of skin on the arm of the patient suffering from psoriasis three months following treatment with the method of the present disclosure.

The method of Example 2 was performed on a female patient aged 59 suffering from severe psoriasis, over a four week period. The autologous composition produced by combining the anti-inflammatory/anti-catabolic component with the platelet-rich plasma component was administered to the female patient in four separate injections of the autologous composition one week apart. The treatments involved intra-dermal injection of the entire lesion site. Dramatic visual changes were observed by four weeks post treatment. The outcome was stable after three months post injection with the effects of psoriasis being eradicated. FIG. 19a is a photograph of the affected area of the female patient's arm prior to treatment. FIG. 19b is a photograph of the affected area of the female patient's arm three months after the fourth injection.

The methods of Example 2 are performed with and without the addition of sodium citrate in preparing the anti-inflammatory/anti-catabolic component on subjects suffering from chronic inflammatory skin diseases such as atopic dermatitis and chronic wounds. The chronic inflammatory skin diseases reduce in severity.

Example 8—Horses, Dogs and Camels

The methods of Example 2 with and without the addition of sodium citrate in preparing the anti-inflammatory/anti-catabolic component are performed on horses, dogs and camels suffering from damaged and/or injured connective tissues. The pain associated with the damaged and/or injured connective tissues reduces in severity.

Although the invention has been described with reference to illustrative embodiments, it is to be understood that the invention is not limited to these precise embodiments. Numerous modifications, variations, and adaptations may be made to the particular embodiments of the invention described above without departing from the scope of the invention. The scope of the claims should not be limited by the preferred embodiments set forth in the examples, but should be given the broadest interpretation consistent with the description as a whole.

REFERENCES

1. Fernandes J. C., J. Martel-Pelletier, and J. P. Pelletier. The role of cytokines in osteoarthritis pathophysiology. *Biorheology* 2002; 39(1-2):237-46.
2. Fredberg U., and K. Stengaard-Pedersen. Chronic tendinopathy tissue pathology, pain mechanisms, and etiology with a special focus on inflammation. *Scand. J. Med. Sci. Sports* 2008 February; 18(1):3-15.
3. Loell I., and I. E. Lundberg. Can muscle regeneration fail in chronic inflammation: a weakness in inflammatory myopathies *J. Intern. Med.* 2011 March; 269(3):243-57.
4. Mirza, Rita E., Millie M. Fang, William J. Ennis, and Timothy J. Koh. Blocking Interleukin-1 Induces a Healing-Associated Wound Macrophage Phenotype and Improves Healing in Type 2 Diabetes. *Diabetes* 2013 July; 62(7): 2579-2587.
5. Eming S. A., T. Krieg, and J. M. Davidson. Inflammation in wound repair: molecular and cellular mechanisms. *J. Invest Dermatol.* 2007; 127:514.
6. Dinarello C. A. Interleukin-1, interleukin-1 receptors and interleukin-1 receptor antagonist. *Int. Rev. Immunol.* 1998; 16(5-6):457-99.
7. Mosmann T. R., H. Cherwinski, M. W. Bond, M. A. Giedlin, and R. L. Coffman. Two types of murine helper T cell clone. I. Definition according to profiles of lymphokine activities and secreted proteins. *J. Immunol.* 1986 Apr. 1; 136(7):2348-57.
8. Brandtzaeg P., L. Osnes, R. Ovsteb, G. B. Jo, A. B. Westvik, and P. Kierulf. Net inflammatory capacity of human septic shock plasma evaluated by a monocyte-based target cell assay: identification of interleukin-10 as a major functional deactivator of human monocytes. *J. Exp. Med.* 1996 Jul. 1; 184(1):51-60.
9. Clarke C. J., A. Hales, A. Hunt, and B. M. Foxwell. IL-10-mediated suppression of TNF-alpha production is independent of its ability to inhibit NF kappa B activity. *Eur. J. Immunol.* 1998 May; 28(5):1719-26.
10. de Waal Malefyt R., C. G. Figdor, R. Huijbens, S. Mohan-Peterson, B. Bennett, J.
Culpepper, W. Dang, G. Zurawski, and J. E. de Vries. Effects of IL-13 on phenotype, cytokine production, and cytotoxic function of human monocytes. Comparison with IL-4 and modulation by IFN-gamma or IL-10. *J. Immunol.* 1993 Dec. 1; 151(11):6370-81.
11. Alvarez R. H., H. M. Kantarjian, and J. E. Cortes. Biology of platelet-derived growth factor and its involvement in disease. *Mayo Clin. Proc.* 2006 September; 81(9):1241-57.
12. Roberts A. B., K. C. Flanders, P. Kondaiah, N. L. Thompson, E. Van Obberghen-Schilling, L. Wakefield, P. Rossi, B. De Crom-Brugghe, U. I. Heine, and M. B. Sporn. Transforming growth factor beta: biochemistry and roles in embryogenesis, tissue repair and remodeling, and carcinogenesis. *Rec. Prog. Horm. Res.* 44:157-197, 1988.
13. Roberts A. B., U. I. Heine, K. C. Flanders, and M. B. Sporn. TGF-beta: Major role in regulation of extracellular matrix. *Ann. N.Y. Acad. Sci.* "Structure, Molecular Biology and Pathology of Collagen," 580:225-232, 1990.
14. Gospodarowicz, D., J. A. Abraham, and J. Schilling. Isolation and characterization of a vascular endothelial cell mitogen produced by pituitary-derived folliculo stellate cells. *Proc. Natl. Acad. Sci. USA* 86, 7311-7315, 1989.
15. Hirata H., T. Nagakura, M. Tsujii, A. Morita, K. Fujisawa, and A. Uchida. The relationship of VEGF and PGE2 expression to extracellular matrix remodeling of the tenosynovium in the carpal tunnel syndrome. *J. Pathol.* 2004 December; 204(5):605-12.
16. Peng H., A. Usas, A. Olshanski, A. M. Ho, B. Gearhart, G. M. Cooper, and J. Huard. VEGF improves, whereas sFlt1 inhibits, BMP2-induced bone formation and bone healing through modulation of angiogenesis. *J. Bone Miner. Res.* 2005 November; 20(11):2017-27.
17. Poutsiaka D. D., B. D. Clark, E. Vannier, and C. A. Dinarello. Production of interleukin-1 receptor antagonist and interleukin-1 beta by peripheral blood mononuclear cells is differentially regulated. *Blood* 1991 Sep. 1; 78(5): 1275-81.
18. Fufa D., B. Shealy, M. Jacobson, et al. Activation of platelet-rich plasma using soluble Type I collagen. *J. Oral Maxillofac. Surg.* 2008; 66:684-90.
19. Mannello F. Serum or plasma samples? The "Cinderella" role of blood collection procedures: preanalytical methodological issues influence the release and activity of circulating matrix metalloproteinases and their tissue inhibitors, hampering diagnostic trueness and leading to misinterpretation. *Arterioscler. Thromb. Vasc. Biol.* 2008 April; 28(4):611-4.

The content of these references is hereby incorporated by reference.

The invention claimed is:

1. A method of treating a mammal suffering from damaged and/or injured connective tissues, chronic tendinosis, chronic muscle tears and/or chronic degenerative joint conditions and skin inflammatory disorders, the method comprising the following steps:
   preparing an anti-inflammatory/anti-catabolic component of an autologous composition comprising IL-1ra, tissue inhibitor of matrix metalloproteinase 1 ("TIMP 1"), and tissue inhibitor of matrix metalloproteinase 2 ("TIMP 2"), the step of preparing the anti-inflammatory/anti-catabolic component comprising the following steps:
      collecting blood from the mammal;
      delivering the blood to a tube;
      incubating the blood at a temperature of from about 37° C. to about 39° C. for about 24 hours, so as to increase the concentration of TIMP 1 therein to greater than 6,500 pg/ml and to increase the concentration of TIMP 2 therein to greater than 4,000 pg/ml;
      centrifuging the blood to separate the blood into a supernatant component and a cellular fraction; and
      collecting the supernatant component of the anti-inflammatory/anti-catabolic component;
   preparing a regenerative component of the autologous composition comprising the following steps:
      collecting blood from the mammal;
      delivering the blood to a tube in the presence of about 4% citric acid;
      centrifuging the blood to separate a platelet rich plasma component from a whole blood; and
      collecting the platelet rich plasma component;
   mixing the supernatant component with the platelet rich plasma component to provide the autologous composition; and
   administering the autologous composition to the mammal.

2. The method according to claim 1, wherein the tube for receiving the blood in the preparation of the anti-inflammatory/anti-catabolic component is a vacutainer tube constructed of glass.

3. The method according to claim 1, wherein the tube for receiving the blood in the preparation of the anti-inflammatory/anti-catabolic component is a vacutainer tube constructed of polystyrene.

4. The method according to claim 1, wherein the step of preparing an anti-inflammatory/anti-catabolic component of the autologous composition comprising IL-1ra and TIMPs further comprises the step of culturing the blood in the presence of $Ca^{++}$ to facilitate IL-1ra production.

5. The method according to claim 4, wherein the blood is cultured with a sterile calcium chloride solution comprising about 0.64 to about 0.72 mM $Ca^{++}$ in a 9:1 proportion by adding the solution using a sterile syringe and needle directly to the tube with autologous physiological fluid before the incubation step.

6. The method of claim 4, further comprising the step of adding sterile air to the tube comprising the blood for increasing IL-1ra production.

7. The method according to claim 1, wherein the supernatant component is divided into aliquots and stored for future use.

8. The method according to claim 1, wherein the supernatant component is divided into aliquots and frozen for future use.

9. The method according to claim 1, wherein the step of delivering the blood to a tube including a quantity of about 4% citric acid comprises providing a ratio of 9.5 parts of whole blood: 0.5 parts of 4% citric acid.

10. The method according to claim 1, wherein a leukocyte buffy coat fraction is added to regenerative component as an additional VEGF source.

11. The method according to claim 1, wherein the step of mixing the supernatant component with the platelet rich plasma component to provide the autologous composition comprises mixing the supernatant component with the platelet rich plasma component in a 1:1 ratio.

12. The method according to claim 1, wherein the mammal is a human.

13. A method of treating damaged and/or injured connective tissues, chronic tendinosis, chronic muscle tears and/or chronic degenerative joint conditions and skin inflammatory disorders in a mammal, the method comprising the following steps:
preparing an anti-inflammatory/anti-catabolic component of an autologous composition comprising IL-1ra and tissue inhibitors of matrix metalloproteinase ("TIMPs"), the step of preparing the anti-inflammatory/anti-catabolic component comprising the following steps:
collecting blood from the mammal;
adding an about 4% sodium citrate solution to a tube;
delivering the blood to the tube;
incubating the blood at a temperature of from about 37° C. to about 39° C. for about 24 hours;
centrifuging the blood to separate the blood into a supernatant component and a cellular fraction; and
collecting the supernatant component of the anti-inflammatory/anti-catabolic component;
preparing a regenerative component of the autologous composition comprising the following steps:
collecting blood from the mammal;
delivering the blood to a tube including a quantity of about 4% citric acid solution;
centrifuging the blood to separate a platelet rich plasma component from the blood;
collecting the platelet rich plasma component;
mixing the supernatant component with the platelet rich plasma component to provide the autologous composition; and
administering the autologous composition to the mammal,
wherein preparing the anti-inflammatory/anti-catabolic component with the about 4% sodium citrate solution significantly decreases MMP9 concentration in the anti-inflammatory/anti-catabolic component and in the autologous composition in comparison to an autologous composition prepared without utilizing the about 4% sodium citrate solution to prepare the anti-inflammatory/anti-catabolic component.

14. The method of claim 13 wherein the 4% sodium citrate solution is added to the tube to provide a ratio of about 0.5:9.5 of the 4% sodium citrate solution to blood upon delivery of the blood to the tube.

15. A method of treating a mammal having damaged and/or injured connective tissues, chronic tendinosis, chronic muscle tears and/or chronic degenerative joint conditions and skin inflammatory disorders, the method comprising:
preparing a first component of an autologous composition by:
admixing blood from the mammal with an amount of about 4% sodium citrate solution to form an admixture,
incubating the admixture at a temperature of from about 37° C. to about 39° C. for about 24 hours, wherein the sodium citrate significantly decreases MMP9 concentration in the admixture in comparison to such an admixture without sodium citrate therein;
centrifuging the thus incubated admixture to separate the admixture into a supernatant component and a cellular fraction; and
collecting the supernatant component as the first component;
preparing a second component of the autologous composition by:
mixing blood from the mammal with a quantity of about 4% citric acid solution;
centrifuging the blood and citric acid mixture to separate a platelet rich plasma component therefrom; and
collecting the platelet rich plasma component;
mixing the first component with the second component to provide the autologous composition; and
administering the autologous composition to the mammal.

\* \* \* \* \*